United States Patent [19]

Fujii et al.

[11] Patent Number: 4,999,378

[45] Date of Patent: Mar. 12, 1991

[54] PHENYLCARBOXYLIC ACID DERIVATIVES

[75] Inventors: Setsuro Fujii, Kyoto; Hiroyuki Kawamura; Shinichi Watanabe, both of Otsu, all of Japan

[73] Assignee: Otsuka Pharmaceutical Company, Limited, Tokyo, Japan

[21] Appl. No.: 372,336

[22] Filed: Jun. 20, 1989

[30] Foreign Application Priority Data

Oct. 20, 1987 [JP] Japan .................. 62-264744
Feb. 26, 1988 [JP] Japan .................. 63-45399

[51] Int. Cl.$^5$ ................................ A61K 31/195
[52] U.S. Cl. ............................ 514/567; 514/539; 514/450; 514/456; 514/466; 514/455; 560/21; 560/45; 562/435; 562/451; 549/375; 549/443
[58] Field of Search ............. 560/45, 21, 45; 562/452, 451; 514/539, 567, 567, 539, 450, 456, 466, 455; 549/375, 443

[56] References Cited

U.S. PATENT DOCUMENTS

| | | | |
|---|---|---|---|
| 2,642,432 | 6/1953 | Clinton et al. | 560/45 |
| 3,738,999 | 6/1973 | Kropcbo et al. | 562/452 |
| 3,763,214 | 10/1973 | Kropcho et al. | 562/452 |
| 3,857,873 | 12/1974 | Schwender et al. | 510/45 |
| 4,094,991 | 6/1978 | Murai et al. | 514/567 |
| 4,109,013 | 8/1978 | Grill et al. | 514/567 |
| 4,154,850 | 5/1979 | Morgan et al. | 514/539 |
| 4,260,816 | 4/1981 | Albright et al. | 562/452 |
| 4,350,822 | 9/1982 | Albright et al. | 562/452 |

FOREIGN PATENT DOCUMENTS 2191487 12/1987 United Kingdom ................ 562/452

OTHER PUBLICATIONS

Chemical Abstracts, vol. 93, No. 19, Nov. 10, 1980; p. 620, No. 185904j, N. Kh. Maksudov et al., "O-Alkylation of Hydroxybenzoic Acids", U2b, Khim. Zh., 1980 (2), 46–50, (Russ).

Primary Examiner—James H. Reamer
Attorney, Agent, or Firm—Wegner, Cantor, Mueller & Player

[57] ABSTRACT

Phenylcarboxylic acid derivatives having the formula:

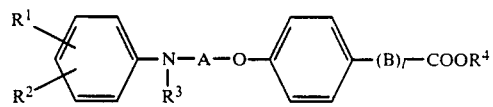

wherein $R^1$ and $R^2$ are each H, halogen, alkyl, haloalkyl, alkanoyl, cycloalkyl, nitro, amino, —O—D—$R^5$ (D is alkylene, $R^5$ is H, amino, morpholino, carboxyl, phthalimido, phenyl, epoxy), substituted or unsubstituted phenoxy, substituted or unsubstituted phenylalkylamino, carboxylalkenyl, or both form alkylenedioxy; $R^3$ is H, —E—$R^6$ (E is alkylene, $R^6$ is H, carboxyl, cyano, OH, phenylalkoxy, or halogen-substituted phenyl, or phenylcarbamoyl), —CO—G—$R^7$ (G is alkylene, $R^7$ is H, substituted or unsubstituted phenylcarbamoyl), substituted or unsubstituted benzoyl, alkenyl, carbamoyl, phenyl, or halophenyl; $R^4$ is H or alkyl; A is alkylene, alkylene condensed with cycloalkyl ring, or alkenylene; B is alkylene or alkenylene; ll is 0 or 1. Said compounds have fatty acid synthesis-inhibitory activity, cholesterol synthesis-inhibitory activity and are useful as antilipidemic agent, prophylactic and treating agent of artherosclerosis, prophylactic and treating agent of obesity, antidiabetics.

10 Claims, No Drawings

PHENYLCARBOXYLIC ACID DERIVATIVES

TECHNICAL FIELD

This invention relates to novel phenylcarboxylic acid derivatives and salts thereof, more particularly, to the compounds having hypolipidemic activity and being useful as a medicament.

TECHNICAL BACKGROUND

There have been known some compounds having hypolipidemic activity, for example, 1,3-disubstituted propanol derivatives disclosed in U.S. Pat. No. 4,073,935, 4,109,013 and 4,144,351, and British Patent 1,516,747, but this invention provides novel phenylcarboxylic acid derivatives and salts thereof which have different structure from these known compounds and are particularly useful as a medicament.

DISCLOSURE OF THE INVENTION

This invention provides phenylcarboxylic acid derivatives and salts thereof, which have the following formula:

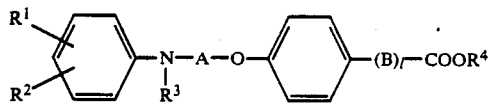

wherein $R^1$ and $R^2$ are each hydrogen atom, a halogen atom, a lower alkyl group, a lower alkyl group having a halogen atom, a lower alkanoyl group, a cyclo(lower)alkyl group, a nitro group, an amino group, a group of the formula: $-O-D-R^5$ (wherein D is a lower alkylene group, $R^5$ is hydrogen atom, an amino group, a morpholino group, a carboxyl group, a phthalimido group, a phenyl group, or a group of the formula:

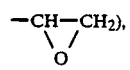

a phenoxy group having optionally a substituent selected from a halogen atom or a lower alkyl group on the phenyl ring, a phenyl(lower)alkylamino group having optionally a lower alkylenedioxy group as a substituent on the phenyl ring, or a lower alkenyl group having a carboxyl group, or both groups form a lower alkylenedioxy group which bond to the adjacent carbon atoms;

$R^3$ is hydrogen atom, a group of the formula: $-E-R^6$ (wherein E is a lower alkylene group, $R^6$ is hydrogen atom, a carboxyl group, a cyano group, a hydroxy group, a phenyl(lower)alkoxy group, a phenyl group having a halogen atom, or a phenylcarbamoyl group having a halogen atom), a group of the formula: $-CO-G-R^7$ (wherein G is a lower alkylene group, $R^7$ is hydrogen atom, a carboxyl group, or a phenylcarbamoyl group having a halogen atom), a benzoyl group having optionally a substituent selected from a lower alkylenedioxy group, a halogen atom or a lower alkyl group on the phenyl ring, a lower alkenyl group, a carbamoyl group, a phenyl group, or a phenyl group having a halogen atom;

$R^4$ is hydrogen atom or a lower alkyl group;

A is a lower alkylene group, a lower alkylene group condensed with a cycloalkyl ring, or a lower alkenylene group;

B is a lower alkylene group or a lower alkenylene group;

l is 0 or 1.

It is assumed that when the compounds of the formula (1) and there salts of this invention are administered, they are esterized with CoA in the living body and inhibit strongly cholesterol- and fatty acids-biosynthetic enzymes and thereby exhibit activity of inhibiting fatty acids-synthesis and activity of inhibiting cholesterolsynthesis, and further, they are well absorbed into the living body and have durable pharmacological activity, higher safety, excellent absorbability and discharging property and also low toxicity. Accordingly, these compounds are useful as a medicament such as hypolipidemic drug, prophylactic and treating agent of artherosclerosis, prophylactic and treating agent of obesity, antidiabetics, and the like.

The groups as defined for $R^1-R^4$, A and B and others in the present specification include specifically the following groups.

The halogen atom includes fluorine, chlorine, bromine and iodine.

The lower alkyl group includes straight chain or branched chain alkyl groups having 1 to 6 carbon atoms, such as methyl, ethyl, propyl, isopropyl, butyl, isobutyl, tertbutyl, pentyl, hexyl, and the like.

The lower alkyl group having a halogen atom includes straight chain or branched chain alkyl groups having 1 to 6 carbon atoms and having 1 to 3 halogen atoms, such as chloromethyl, bromomethyl, iodomethyl, fluoromethyl, dichloromethyl, dibromomethyl, difluoromethyl, trichloromerhyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2trichloroethyl, 3-fluoropropyl, 3,3,3-trichloropropyl, 4chlorobutyl, 5-chloroheptyl, 6-chlorohexyl, 3-chloro-2-methylpropyl, and the like.

The lower alkancyl group includes straight chain or branched chain alkanoyl groups having 1 to 6 carbon atoms, such as formyl, acetyl, propionyl, butyryl, isobutyryl, pentanoyl, hexanoyl, and the like.

The cyclo(lower)alkyl group includes cycloalkyl groups having 3 to 8 carbon atoms, such as cyclopropyl, cyclobutyl, cyclopentyl, cyclohexyl, cycloheptyl, cyclooctyl, and the like.

The lower alkylene group includes straight chain or branched chain alkylene groups having 1 to 6 carbon atoms includes methylene, ethylene, trimethylene, tetramethylene, pentamethylene, hexamethylene, 2,2-dimethyltrimethylene, 2-methyltrimethylene, methylmethylene, and the like.

The phenoxy group having optionally a substituent selected from a halogen atom or a lower alkyl group on the phenyl ring includes phenoxy, phenoxy groups having a halogen substituent on the phenyl ring such as 2-chlorophenoxy, 3-chlorophenoxy, 4-chlorophenoxy, 2-fluorophenoxy, 3-fluorophenoxy, 4-fluorqphenoxy, 2-bromophenoxy, 3-bromophenoxy, 4-bromophenoxy, 2-iodophenoxy, 3-iodophenoxy, 4-iodophenoxy, etc., and phenoxy groups having a substituent of an alkyl group having 1 to 6 carbon atoms such as 2-methylphenoxy, 3-methylphenoxy, 4-methylphenoxy, 2-ethylphenoxy, 3-propylphenoxy, 4-isopropylphenoxy, 4-tertbutylphenoxy, 2-pentylphenoxy, 3-hexylphenoxy, 4-hexylphenoxy, etc.

The phenyl(lower)alkylamino group having optionally a lower alkylenedioxy group as a substituent on the phenyl ring includes phenylalkylamino groups having optionally an alkylenedioxy group having 1 to 4 carbon atoms on the phenyl ring wherein the alkyl moiety is a straight chain or branched chain alkyl having 1 to 6 carbon atoms, such as benzylamino, 2-phenylethylamino, 3-phenylpropylamino, 1-phenylethylamino, 4-phenylbutylamino, 5-phenylpentylamino, 6-phenylhexylamino, 2,3-methylenedioxybenzylamino, 3,4-methylenedioxybenzylamino, 2-(3,4-methylenedioxyphenyl)-ethylamino, 2,3-ethylenedioxybenzylamino, 3,4-ethylenedioxybenzylamino, 6-(2,3-ethylenedioxyphenyl)hexylamino, 2,3-trimethylenedioxybenzylamino, 3,4-trimethylenedioxybenzylamino, 3-(3,4-trimethylenedioxyphenyl)propylamino, 2,3-tetramethylenedioxybenzylamino, 3,4-tetramethylenedioxybenzylamino, 1-(3,4-tetramethylenedioxyphenyl)ethylamino, and the like.

The lower alkenyl group having a carboxyl group includes straight chain or branched chain alkenyl groups having 1 to 6 carbon atoms, such as 2-carboxyvinyl, 3-carboxyallyl, 2-carboxypropenyl, 3-carboxy-2-butenyl, 4-carboxy-4-methyl-3-butenyl, 2-carboxy-1-pentenyl, 4-carboxy-3-hexenyl, and the like.

The lower alkylenedioxy group includes alkylenedioxy groups having 1 to 4 carbon atoms, such as methylenedioxy, ethylenedioxy, trimethylenedioxy, tetramethylenedioxy, and the like.

The phenyl(lower)alkoxy group includes phenylalkoxy groups wherein the alkoxy moiety has straight chain or branched chain and has 1 to 6 carbon atoms, such as benzyloxy, 2-phenylethoxy, 3-phenylpropoxy, 4-phenylbutoxy, 1,1-dimethyl-2-phenylbutoxy, 5-phenylpentyloxy, 6-phenylhexyloxy, and the like.

The phenyl group having a halogen atom includes phenyl groups having a halogen atom as a substituent, such as 2-chlorophenyl, 3-chlorophenyl, 4-chlorophenyl, 2-fluorophenyl, 3-fluorophenyl, 4-fluorophenyl, 2-bromophenyl, 3bromophenyl, 4-bromophenyl, 2-iodophenyl, 3-iodophenyl, 4-iodophenyl, and the like.

The phenylcarbamoyl group having a halogen atom includes phenylcarbamoyl groups having a halogen atom as a substituent on the phenyl ring, such as 2-chlorophenylcarbamoyl, 3-chlorophenylcarbamoyl, 4-chlorophenylcarbamoyl, 2-fluorophenylcarbamoyl, 3-fluorophenylcarbamoyl, 4-fluorophenylcarbamoyl, 2-bromophenylcarbamoyl, 3-bromophenylcarbamoyl, 4-bromophenylcarbamoyl, 2-iodophenylcarbamoyl, 3-iodophenylcarbamoyl, 4-iodophenylcarbamoyl, and the like.

The benzoyl group having optionally a substituent selected from a lower alkylenedioxy group, a halogen atom or a lower alkyl group on the phenyl ring includes benzoyl groups having optionally an alkylenedioxy group having 1 to 4 carbon atoms, a halogen atom, or a straight chain or branched chain alkyl group having 1 to 6 carbon atoms as a substituent on the phenyl ring, such as benzoyl, 2,3-methylenedioxybenzoyl, 3,4-methylenedioxybenzoyl, 2,3-ethylenedioxybenzoyl, 3,4-ethylenedioxybenzoyl, 2,3-trimethylenedioxybenzoyl, 3,4-trimethylenedioxybenzoyl, 2,3-tetramethylenedioxybenzoyl, 3,4-tetramethylenedioxybenzoyl, 2-chlorobenzoyl, 3-chlorobenzoyl, 4-chlorobenzoyl, 2-bromobenzoyl, 3-bromobenzoyl, 4-bromobenzoyl, 2-fluorobenzoyl, 3-fluorobenzoyl, 4-fluorobenzoyl, 2-iodobenzoyl, 3-iodobenzoyl, 4-iodobenzoyl, 2-methylbenzoyl, 3-methylbenzoyl, 4-methylbenzoyl, 2-ethylbenzoyl, 3-propylbenzoyl, 4-isopropylbenzoyl, 4-tert-butylbenzoyl, 2-pentylbenzoyl, 3-hexylbenzoyl, 4-hexylbenzoyl, and the like.

The alkenyl group includes straight chain or branched chain alkenyl groups having 2 to 6 carbon atoms, such as vinyl, propenyl, allyl, isopropenyl, 1-butenyl, 4-pentenyl, 2-ethylallyl, 3-hexenyl, and the like.

The lower alkylene group condensed with a cycloalkyl ring includes alkylene groups having 2 to 6 carbon atoms which are condensed with a cycloalkyl ring having 3 to 8 carbon atoms, such a 1,2-cyclopropylene, 1,2-cyclobutylene, 1,3-cyclobutylene, 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene, 1,4-cycloheptylene, 1,2-cyclooctylene, 1,3-cyclooctylene, 1,4-cyclooctylene, 1,5-cyclooctylene, 5-methylenecyclooctyl, 4-ethylenecycloheptyl, 3-trimethylenecyclohexyl, 2-tetramethylenecycloheptyl, 2-pentamethylenecyclobutyl, 2-methylenecyclopropyl, 2-ethylenecyclopropylmethyl, 2-methylenecycloheptyl, 4-methylenecyclohexylmethyl, and the like.

The lower alkenylene group includes straight chain or branched chain alkenylene groups having 2 to 6 carbon atoms, such as vinylene, propenylene, 1-methylvinylene, 2-butenylene, 3-pentenylene, 2-hexenylene, and the like.

The phenylcarboxylic acid derivative of the formula (1) of this invention can be prepared by various processes using various starting compounds. The examples of the processes are illustrated below with reference to reaction schemes.

[Reaction Scheme-1]

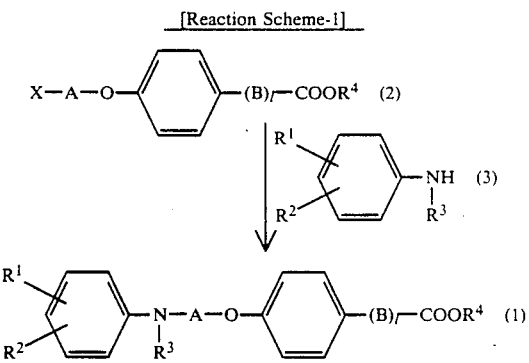

wherein $R^1$, $R^2$, $R^3$, $R^4$, A, B and l are as defined above, and X is a halogen atom, a lower alkanesulfonyloxy group having optionally a substituent, or an arylsulfonyloxy group having optionally a substituent.

According to the above Reaction Scheme-1, the compound of the formula (2) and the compound of the formula (3) are reacted in an appropriate solvent in the presence of a basic compound to give the desired compounds of the formula (1) of this invention.

In the compound of the above formula (2), the halogen atom shown as X includes the same as defined above, the lower alkanesulfonyloxy group having optionally a substituent includes alkanesulfonyloxy groups having 1 to 6 carbon atoms and being optionally substituted by a halogen atom, such as methanesulfonyloxy, ethanesulfonyloxy, propanesulfonyloxy, trifluoromethanesulfonyloxy, etc., and the arylsulfonyloxy group having optionally a substituent includes arylsulfonyloxy groups being optionally substituted by an alkyl group having 1 to 6 carbon atoms, a halogen atom or a nitro group, such as benzenesulfonyloxy, toluenesulfonyloxy, p-chlorobenzenesulfonyloxy, p-nitrobenzenesulfonyloxy, etc.

In the process of the above Reaction Scheme-1, the inert solvent includes various solvents which do not give any bad effect on the reaction, for example, ethers such as diethyl ether, tetrahydrofuran (THF), dioxane, etc.; halogenated hydrocarbons such as dichloromethane, dichloroethane, chloroform, carbon tetrachloride, etc.; aromatic hydrocarbons such as benzene, toluene, xylene, etc.; amines such as pyridine, piperidine, trierhylamine, etc.; aliphatic hydrocarbons such as hexane, heptane, etc.; alcohols such as methanol, ethanol, propanol, etc.; aprotic polar solvents such as dimethylformamide (DMF), dimethylacetamide (DMA), dimethylsulfoxide (DMSO), hexamethylphosphoric triamide (HMPA), etc.; carbon disulfide; and the like. The basic compound includes, for example, organic basic compounds such as tertiary amines (e.g. triethylamine, pyridine, etc.) and inorganic basic compounds such as alkali metal carbonates (e.g. sodium carbonate, potassium carbonate, etc.), alkali metal hydrogen carbonates (e.g. sodium hydrogen carbonate, potassium hydrogen carbonate, etc.), alkali metal hydroxides (e.g. sodium hydroxide, potassium hydroxide, etc.), alkali metals (e.g. sodium, potassium, etc.), alkali metal hydrides (e.g. sodium hydride, etc.).

The compound of the formula (3) is usually used in an amount of about 1 to 5 moles, preferably about 1 to 2 moles, to 1 mole of the compound of the formula (2), and the basic compound is usually used in an amount of about 1 to 100 moles, preferably about 1 to 3 moles, to 1 mole of the compound of the formula (2).

The above reaction is usually carried out at about 0° to 200° C., preferably at room temperature—about 120° C., for about 20 minutes to about 72 hours, preferably about 30 minutes to about 24 hours.

Besides, when the reactive nitrogen atom in the above compound (3) forms amido bond with $R^3$, it is preferable to react previously the above compound (3) with a basic compound such as an alkali metal or an alkali metal hydride and then to react the resulting compound with the compound (2).

[Reaction Scheme-2]

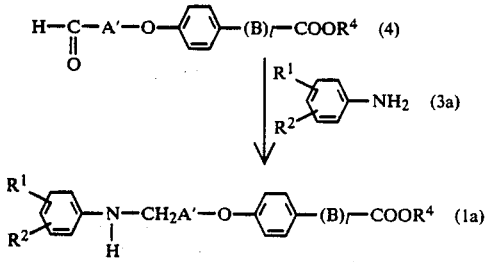

wherein $R^1$, $R^2$, $R^4$, B and l are as defined above, and A' is the same as A except that it has one smaller carbon number in the main chain thereof.

According to the above Reaction Scheme-2, the compound of the formula (4) and the compound of the formula (3a) are reacted in an appropriate inert solvent in the presence or absence of a dehydrating agent to produce a Schiff's base and then the resulting compound is reduced to give the desired compound of the formula (la) of this invention.

In the above process, the inert solvent includes various solvents which do not give any bad effect on the reaction, for example, alcohols such as methanol, ethanol, propanol, etc.; halogenated hydrocarbons such as dichloromethane, dichloroethane, chloroform, etc.; aromatic hydrocarbons such as benzene, toluene, xylene, etc.; ethers such as diethyl ether, tetrahydrofuran, dioxane, etc.; amines such as pyridine, piperidine, triethylamin,, etc.; aliphatic hydrocarbons such as hexane, heptane, etc.; acetic acid esters such as ethyl acetate, methyl acetate, etc.; aprotic polar solvents such as DMF, DMSO, HMPA, etc.; and the like.

The dehydrating agent includes various conventional dehydrating agents, for example, drying agents used for dehydrating solvents such as molecular sieves, silica gel, calcium chloride, sodium sulfate, magnesium sulfate, etc.; Lewis acids such as anhydrous aluminum chloride, stannic chloride, titanium tetrachloride, boron trichloride, boron trifluoride-ethyl ether complex, zinc chloride, etc.; inorganic acids such as hydrochloric acid, nitric acid, sulfuric acid, etc.; organic acids such as trichloroacetic acid, trifluoroacetic acid, methanesulfonic acid, acetic acid, etc.; and other acid type ion exchange resins; and the like.

The above reaction for producing Schiff's base, the compound of the formula (3a) is usually used in an amount of about 1 to 3 moles, preferably equivalent amount, to 1 mole of the compound of the formula (4), and the reaction is usually carried out at about −20° to 180° C., preferably at room temperature—about 100° C., for about 10 minutes to about 24 hours, preferably about 30 minutes to about 3 hours.

The subsequent reducing reaction is carried out by a conventional method, for instance, by using an appropriate reducing agent or by a conventional catalytic reduction.

In the method using an appropriate reducing agent, the reducing agent includes, for example, metal hydrides such as sodium cyanoboron hydride, sodium boron hydride, lithium aluminum hydride, etc.; borane, and the like. These reducing agents are usually used in an amount of about 0.1 to 100 moles, preferably about 0.25 to 50 moles, to 1 mole of the compound of the formula (4), and the reducing reaction using a reducing agent is usually carried out at about −20° to 180° C., preferably at about 0° to 60° C., for about 10 minutes to about 24 hours, preferably about 30 minutes to about 3 hours.

Besides, the catalytic reduction can be carried out in an inert solvent with an appropriate catalyst. The catalyst used for the catalytic reduction includes, for example, platinum catalysts such as platinum oxide, platinum black, platinum wire, platinum plate, sponge platinum, colloidal platinum, etc.; palladium catalysts such as palladium black, palladium chloride, palladium oxide, palladium-carbon, palladium-barium sulfate, palladium-carbon barium, sponge palladium, etc.; nickel catalysts such as reduced nickel, nickel oxide, Raney nickel, etc.; cobalt catalysts such as reduced cobalt, Raney cobalt, etc.; iron catalysts such as reduced iron, Raney iron, etc.; copper catalysts such as reduced copper, Raney copper, etc.; and the like. The inert solvent includes various solvents which do not give any bad effect on the reaction, for example, ethers such as dimethyl ether, diethyl ether, THF, dioxane, anisole, etc.; halogenated hydrocarbons such as dichloromethane, dichloroethane, chloroform, carbon tetrachloride, etc.; aromatic hydrocarbons such as benzene, toluene, xylene, etc.; amines such as pyridine, piperidine, triethylamine, etc.; aliphatic hydrocarbons such as hexane, heptane, octane, etc.; alcohols such as methanol, ethanol, propanol, etc.; acetic acid esters such as ethyl acetate, methyl acetate, etc.; aprotic polar solvents such as DMF, DMSO, HMPA, etc.; carbon disulfide; water; and the like, or a mixture of water with the above organic solvents The catalyst for the catalytic reduction is usually used in an amount of about 0.1 to 10 moles, preferably about 0.1 to 1 mole, to 1 mole of the starting compound of the formula (4). The reaction temperature is usually in the range of about 0° to 200° C., preferably about 0° to 100° C., and the reaction is usually completed in about 30 minutes to about 8 hours, preferably about 30 minutes to about 6 hours.

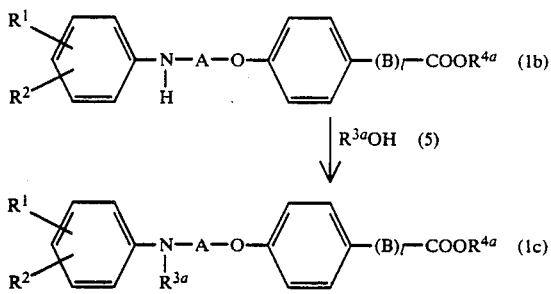

[Reaction Scheme-3]

wherein $R^1$, $R^2$, A, B and l are as defined above, $R^{3a}$ is a group of the formula: —CO—G—$R^7$ (wherein G and $R^7$ are as defined above), or a benzoyl group having oprionally a lower alkylenedioxy group, a halogen atom, or a lower alkyl group as a substituent on the phenyl ring, and $R^{4a}$ is a lower alkyl group.

According to the above Reaction Scheme-3, the amine compound of the formula (1b) and the carboxylic acid compound of the formula (5) or a compound activated at the carboxyl group thereof are reacted by a conventional amido bond producing reaction to give the desired compound of the formula (1c) of this invention.

The amido bond producing reaction can easily be carried out by the following various amido bond producing processes.

(a) a process using a condensation agent, i.e. a process of reacting the carboxylic acid compound (5) and the amine compound (1b) in the presence of a condensation agent, (b) a mixed acid anhydride process, i.e. a process of reacting the carboxylic acid compound (5) with an alkylhalocarboxylic acid to form a mixed acid anhydride and reacting the resultant with the amine compound (1b), (c) an activated ester process, i.e. a process of converting the carboxylic acid compound (5) into an activated ester, such as p-nitrophenyl ester, N-hydroxysuccinimide ester, 1-hydroxybenzotriazole ester, etc., and reacting the resultant with the amine compound (1b), (d) a carboxylic anhydride process, i.e. a process of converting the carboxylic acid compound (5) into a carboxylic anhydride by treating it with a dehydrating agent such as acetic anhydride, and reacting the resultant with the amine compound (1b), (e) a process at a high temperature under high pressure, i.e. a process of reacting an ester of the carboxylic acid compound (5) with a lower alcohol and the amine compound (1b) at a high temperature under high pressure, (f) an acid halide process, i.e. a process of converting the carboxylic acid compound (5) into an acid halide compound, i.e. a carboxylic acid halide, and reacting the resultant with the amine compound (1b).

The above acid anhydride process is explained in detail below. This process can be carried out by reacting the compound of the formula (1b) with an acid anhydride corresponding to $R^{3a}$ to be introduced into said compound (including intramolecular acid anhydride) in an appropriate solvent. The acid anhydride is preferably used at least in about equimolar amount, preferably about 1 to 3 moles, to 1 mole of the compound of the formula (1b). The solvent includes various inert solvents which are usually used in this kind of reaction, specifically halogenated hydrocarbons such as methylene chloride, chloroform, dichloromethane, dichloroethane, etc.; aromatic hydrocarbons such as benzene, toluene, xylene, etc.; ethers such as diethyl ether, dioxane, THF, dimethoxyethane, etc.; DMF; DMSO; HMPA; acetonitrile; pyridine; and the like. This reaction is usually carried out at about −30° to 100° C., preferably at room temperature to about 80° C., for about 20 minutes to about 20 hours. Besides, the above reaction may advantageously be carried out in the presence of a basic compound. The basic compound include, for example, organic bases such as tertiary amines (e.g. pyridine, triethylamine, N,N-dimethylaniline, etc.); inorganic bases (e.g. sodium hydrogen carbonate, potassium carbonate, etc.); sodium acetate; and the like.

The above acid halide process is explained in detail. This reaction can be carried out by reacting the compound of the formula (1b) with an acyl halide of the formula: $R^{3a}$-Y (wherein $R^{3a}$ is as defined above, and Y is a halogen atom) in an appropriate solvent in the presence of a dehydrohalogenation agent. The dehydrohalogenation agent includes conventional agents, for example, sodium hydrogen carbonate, sodium carbonate, potassium carbonate, pyridine, triethylamine, and the like. The solvent includes also conventional ones, for example, benzene, chloroform, methylene chloride, dioxane, THF, and the like. The acyl halide used in the above reaction is usually used at least in about equimolar amount, preferably about 1 to 3 moles, to 1 mole of the compound (1b). The reaction temperature is usually in the range of −30° to 100° C., preferably room temperature to about 80° C., and the reaction is usually completed in about 20 minutes to about 20 hours.

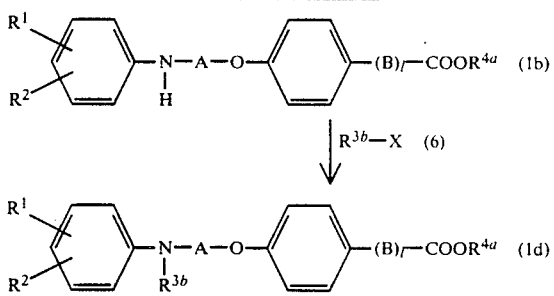

[Reaction Scheme-4]

wherein $R^1$, $R^2$, $R^{4a}$, A, B, l and X are as defined above, and $R^{3b}$ is a group of the formula: —E—$R^6$ (wherein E and $R^6$ are as defined above), a lower alkenyl group or a phenyl group having a halogen atom.

According to the above Reaction Scheme-4, the compound of the formula (1b) and the compound of the formula (6) are reacted to give the desired compound of the formula (1d) of this invention.

The reaction is carried out in the same manner as the reaction of the compound (2) and the compound (3) in the above Reaction Scheme-1.

[Reaction Scheme-5]

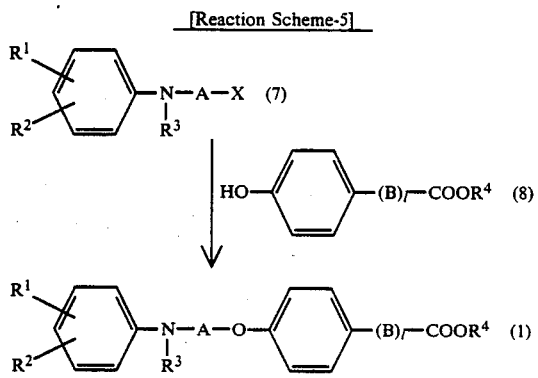

wherein $R^1$, $R^2$, $R^3$, $R^4$, A, B, 1 and X are as defined above.

According to the above Reaction Scheme-5, the compound of the formula (7) and the compound of the formula (8) are reacted in the same manner as in the reaction of the compound (2) and the compound (3) as in the above Reaction Scheme-1 to give the desired compound of the formula (1) of this invention.

[Reaction Scheme-6]

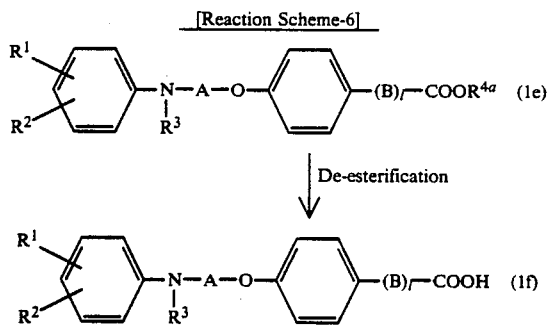

wherein $R^1$, $R^2$, $R^3$, $R^{4a}$, A, B and 1 are as defined above.

According to the above Reaction Scheme-6, the compound of the formula (1e) of this invention is subjected to de-esterification to give the desired compound of the formula (1f) of this invention.

The de-esterification reaction is carried out by reacting the compound of the formula (1e) with an acidic compound or a basic compound in an appropriate inert solvent.

In the process of the above Reaction Scheme-6, the inert solvent include various solvents which do not give any bad effect on the reaction, for example, the same as used in the catalytic reduction in the above Reaction Scheme-2.

The acidic compound includes, for example, Lewis acids such as anhydrous aluminum chloride, stannic chloride, titanium tetrachloride, boron trichloride, boron trifluoride-ethyl ether complex, zinc chloride, etc.; inorganic acids such as hyrochloric acid, nitric acid, sulfuric acid, etc.; organic acids such as trichloroacetic acid, trifluoroacetic acid, methanesulfonic acid, acetic acid, etc.; acid type ion exchange resins; and the like. Besides, the basic compound includes, for example, organic bases such as trialkylamines (e.g. triethylamine, tributylamine, etc.), pyridine, picoline, 1,5-diazabicyclo[4.4.3.0]nonene-5 (DBN), 1,8-diazabicyclo[5.4.0]undecene-7 (DBU), 1,4-diazabicyclo[2.2.2]octane (DABCO), etc.; and inorganic bases such as alkali metal hydroxides (e.g. sodium hydroxide, potassium hydroxide, etc.), alkali metal carbonates (e.g. sodium carbonate, potassium carbonate, etc.); and alkali metal hydrogen carbonates (e.g. sodium hydrogen carbonate, potassium hydrogen carbonate, etc.).

The above acidic compound and basic compound are usually used in an amount of about 1 to 100 moles, preferably about 1 to 20 moles, to 1 mole of the compound of the formula (1e). The abcve reaction is usually carried out at about $-20°$ to $80°$ C., preferably about $-10°$ to $60°$ C., for about 30 minutes to about 48 hours, preferably about 1 to 24 hours.

The desired compounds of this invention can be prepared by the processes shown in the above reaction schemes.

The thus-prepared compounds of the formula (1) of this invention may be subjected to conventional reactions in order to convert the groups of $R^1$, $R^2$, $R^3$ and B to various other groups within the definitions in the formula (1).

For instance, when $R^1$ and/or $R^2$ are a nitro group, these may be converted into an amino group by subjecting to reduction.

This reducing reaction is usually carried out by catalytic reduction or a reduction using an appropriate reducing agent as in the above Reaction Scheme-2.

When $R^1$ and/or $R^2$ are an amino group, the compound of this invention having said amino group is reacted with a phenyl(lower)alkanal having a lower alkylenedioxy group on the phenyl ring to give a Schiff's base, and the resultant is subjected to the reducing reaction to give a compound of this invention wherein $R^1$ and/or $R^2$ are a phenyl(lower)alkylamino group having a lower alkylenedioxy group on the phenyl ring.

This reaction can be carried out under the same conditions as in the reaction of the compound (4) and the compound (3a) in the above Reaction Scheme-2.

Besides, when $R^1$ and/or $R^2$ are a phthalimido group, these groups can be converted into an amino group by subjecting the compound to a hydrazinolysis by reacting it with hydrazine or a hydrazine derivative without solvent or in an inert solvent.

Besides, when $R^3$ is a benzyloxy group, it can be converted into a hydroxy group by reduction thereof. This reduction can be carried out by a conventional method, for instance, by the same catalytic reduction as used in the above Reaction Scheme-2.

Besides, when $R^3$ is a carboxyl group, it can be converted into a phenylcarbamoyl group having a halogen atom by reacting the compound with aniline having a halogen atom. This amido bond producing reaction can be carried out by a conventional method, for instance, by the same method as used in the above Reaction Scheme-3.

Besides, when B is an alkenylene group, it can be converted into an alkylene group by reduction thereof. This reducing reaction can be carried out by a conventional method, for instance, by the same catalytic reduction or reduction using a reducing agent as in the above Reaction Scheme-2.

Moreover, in order to introduce a specific $R^3$ group to the compound (1b) of this invention, the following various processes can be employed.

For instance, by reacting the compound of the formula (1b) and a cyanate in an appropriate inert solvent in the presence of an acidic compound, there is obtained a compound of this invention wherein $R^3$ is a carbamoyl group. The inert solvent used therein includes various solvents which do not give any bad effect on the reaction, for example, aromatic hydrocarbons such as benzene, toluene, xylene, etc.; halogenated hydrocarbons such as dichloromethane, dichloroethane, chloroform, carbon teterchloride, etc.; ethers such as diethyl ether, THF, dioxane, etc.; aliphatic hydrocarbons such as hexane, heptane, etc.; aprotic polar solvents such as DMF, DMSO, HMPA, etc.; and the like. The acidic compound includes, for example, organic acids such as trifluoroacetic acid, trichloroacetic acid, methanesulfonic acid, acetic acid, etc.; inorganic acids such as hydrochloric acid, nitric acid, sulfuric acid, etc.; Lewis acids such as anhydrous aluminum chloride, stannic chloride, titanium tetrachloride, boron trichloride, boron trifluoride-ethyl ether complex, zinc chloride, etc.; acid type ion exchange resins., and the like. The cyanate used therein includes, for example, sodium cyanate, potassium cyanate, and the like.

In the above reaction, the cyanate is usually used in an amount of about 1 to 30 moles, preferably about 1 to 3 moles, to 1 mole of the compound of the formula (1b). The acidic compound is usually used in an amount of about 1 to 30 moles, preferably about 1 to 3 moles, to 1 mole of the compound of the formula (1b). The reaction is usually carried out at about 0° to 100° C., preferably at room temperature to about 60° C., for about 30 minutes to about 24 hours, preferably about 1 to 3 hours.

Besides, the compound of the formula (1b) and an $\alpha,\beta$-unsaturated carboxylic acid or an ester thereof are reacted in the presence or absence of an appropriate solvent to give a compound wherein $R^3$ is a lower alkyl group having a carboxyl group. The inert solvent used therein includes various solvents which do not give any bad effect on the reaction, for example, aromatic hydrocarbons such as benzene, toluene, xylene, etc.; halogenated hydrocarbons such as methylene chloride, chloroform, dichloromethane, dichloroethane, etc.; ethers such as diethyl ether, dioxane, THF, etc.; aliphatic hydrocarbons such as hexane, heptane, etc.; aprotic polar solvents such as DMF, DMSO, HMPA, etc.; and the like.

In the above reaccion, the $\alpha,\beta$-unsaturated carboxylic acid or an ester thereof is usually used in an amount of about 1 to 100 moles, preferably about 1 to 10 moles, to 1 mole of the compound of the formula (1b). The reaction is usually carried out at about 0° to 200° C., preferably at room temperature to about 150° C., for about 30 minutes to about 48 hours, preferably about 1 to 24 hours.

In the above Reaction Schemes-1 to -6, the starting compounds of the formulae (2), (3), (3a), (4), (7) and (8) include novel compounds, which are prepared by the processes as shown in the following Reaction Schemes-7 to -11.

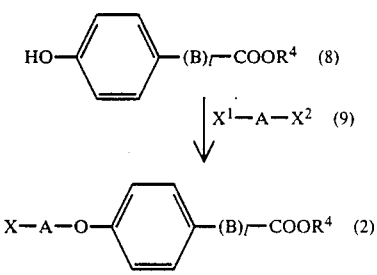

[Reaction Scheme-7]

wherein $R^4$, A, B, l and X are as defined above, and $X^1$ and $X^2$ are each the same as X.

According to the above Reaction Scheme-7, the compound of the formula (8) and the compound of the formula (9) are reacted to give a compound of the formula (2).

This reaction can be carried out in the same manner as in the reaction of the compound (2) and the compound (3) in Reaction Scheme-1.

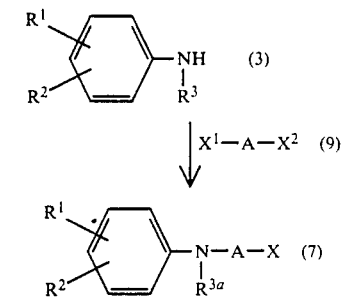

[Reaction Scheme-8]

wherein $R^1$, $R^2$, $R^3$, A, $X^1$, $X^2$ and X are as defined above.

According to the above Reaction Scheme-8, the compound of the formula (3) and the compound of the formula (9) are reacted to give the compound of the formula (7).

This reaction can be carried out under the same conditions as used in the reaction of Reaction Scheme-7.

Besides, the compound of the formula (7) can also be prepared by the following specific method.

The specific method for preparing the compound (7) is, for example, a process comprising reacting a compound of the formula (3) and an $\alpha,\beta$-unsaturated carboxylic acid or an ester thereof or a malonic acid diester derivative under the same conditions as used in the reaction of the compound of the formula (1b) and an $\alpha,\beta$-unsaturated carboxylic acid or an ester thereof as mentioned hereinbefore, subjecting the resulting carboxylic acid derivative to a conventional reduction to convert into a compound having a hydroxy group, and further converting the hydroxy group into a group X by a conventional method, by which the compound of the formula (7) is prepared.

The reduction for converting the carboxylic acid derivative into the compound having a hydroxy group is usually carried out by a conventional method, for example, under the same conditions as in the reduction using an appropriate reducing agent as in Reaction Scheme-2.

The reaction for converting the compound having a hydroxy group into the compound having the corresponding X group is carred out by reacting the compound having a hydroxy group with a sulfonic acid compound or a reactive derivative thereof at the sulfo group or a halogenating agent in a solvent.

The reaction of the compound having a hydroxy group with the sulfonic acid compound or a reactive derivative thereof at the sulfo group is carried out by reacting the compound having a hydroxy group with a sulfonic acid compound corresponding to the above sulfonyloxy group of X group or a reactive derivative thereof at the sulfo group (e.g. halides such as chloride or bromide, acid anhydrides, etc.). The solvent used therein include, for example, aromatic hydrocarbons such as benzene, toluene, etc.; ethers such as diethyl ether, tetrahydrofuran, etc.; halogenated hydrocarbons such as methylene chloride, chloroform, dichloroethane, etc.; aprotic polar solvents such as dimethylformamide, dimethylsulfoxide, hexamethylphosphoric triamide, etc.; acetonitrile; and the like.

The above sulfonic acid compound or a reactive derivative thereof at the sulfo group is usually used in an amount of at least equimolar, preferably about 1 to 1.5 mole, to 1 mole of the compound having a hydroxy group. This reaction is preferably carried out in the presence of a basic compound. The basic compound includes inorganic basic compounds such as alkali metal hydroxides (e.g. sodium hydroxide, potassium hydroxide, etc.), alkali metal carbonates or hydrogen carbonates (e.g. sodium carbonate, potassium carbonate, sodium hydrogen carbonate, etc.); and organic basic compounds such as triethylamine, pyridine, N,N-dimethylaniline, 1,5-diazabicyclo[4.3.0]nonene-5 (DBN), 1,4-diazabicyclo[2.2.2]octane (DABCO), 1,8-diazabicyclo[5.4.0]undecene-7 (DBU), among them, the organic basic compounds are preferable. This reaction is usually carried out at about $-10°$ to $100°$ C., preferably about $0°$ C. to room temperature, for 1 to 20 hours, preferably about 1 to 10 hours.

The compound having an X group wherein X is a halogen atom can be prepared by reacting a compound having a hydroxy group with a halogenating agent. The halogenating agent used in this reactic,n includes, for example, halogen molecules such as chlorine, bromine, iodine, etc.; thionyl halides such as thionyl chloride, thionyl bromide, etc. The reaction is usually carried out in a solvent. The solvent includes, for example, halogenated hydrocarbons such as methylene chloride, 1,2-dichloroethane, chloroform, etc.; ethers such as tetrahydrofuran, dioxane, etc.; and the like. The halogenating agent is usually used in an amount of at least equimolar, preferably about 1 to 2 moles, to 1 mole of the compound having a hydroxy group. The reaction is usually carried out at about $-10°$ to $100°$ C., preferably about $0°$ to $50°$ C., for about 1 to 20 hours, preferably about 1 to 10 hours.

Besides, the compound of the formula (7) can be prepared by reacting a compound of the formula (3a) and a compound having a carbonyl group and further having a carboxylic acid group or an ester group at the terminal under the same conditions as in Reaction Scheme-2 to form a Schiff's base, reducing the resultant, converting the carboxylic acid group or an ester group at the terminal into a hydroxy group by reducing in the same manner as described hereinbefore, followed by converting the group to the X group.

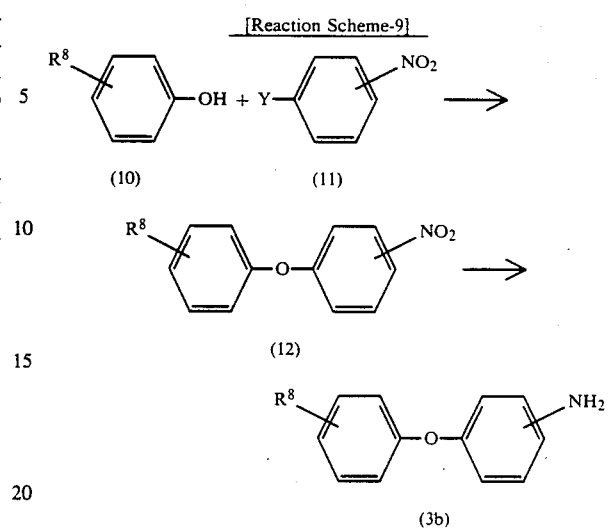

wherein Y is a halogen atom, and $R^8$ is hydrogen atom, a halogen atom, or a lower alkyl group.

According to the above Reaction Scheme-9, the compound of the formula (10) and the compound of the formula (11) are reacted in an inert solvent in the presence of a basic compound (an ether bond producting reaction) and subjecting the resulting compound of the formula (12) to reduction to give the compound of the formula (3b).

The reaction of the compound (10) and the compound (11) is carried out in the same manner as in the reaction of the compound (7) and the compound (8) in Reaction Scheme-5.

Besides, the reduction of the compound (12) thus obtained is carried out by the same manner as in Reaction Scheme-2 or by using stannous chloride as a reducing catalyst under the same conditions.

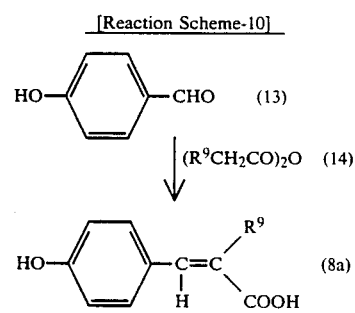

wherein $R^9$ is hydrogen atom or a lower alkyl group.

According to the above Reaction Scheme-10, the compound of the formula (13) is reacted with an aliphatic carboxylic acid anhydride of the formula (14) or an alkali metal salt (e.g. sodium salt or potassium salt) thereof under heating (Parkinson reaction) to give the compound of the formula (8a).

In this reaction, the compound (14) or a salt thereof is usually used in an amount of about 1 to 100 moles, preferably about 1 to 20 moles, to 1 mole of the compound (13). The reaction temperature is usually in the range of about $0°$ to $200°$ C., preferably room temperature to about $150°$ C., and the reaction period is in the range of about 30 minutes to about 96 hours, preferably about 1 to 48 hours.

[Reaction Scheme-11]

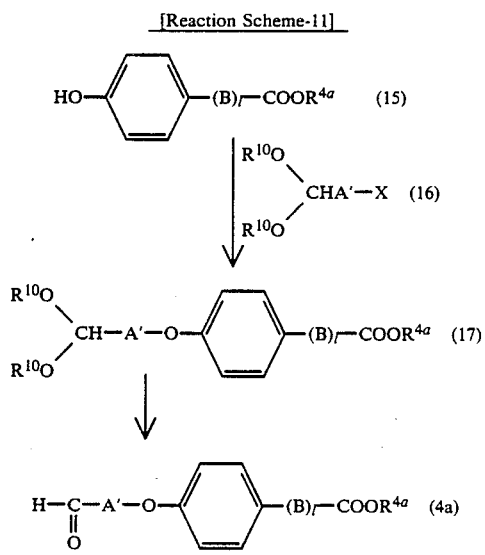

wherein $R^{4a}$, A', B, l and X are as defined above, and $R^{10}$ is a lower alkyl group.

According to the above Reaction Scheme-11, the compound of the formula (15) and the compound of the formula (16) are reacted to give the compound of the formula (17), and the compound (17) is subjected to a de-acetal reaction to give the compound of the formula (4a).

The above reaction for preparing the compound (17) is carried out in the same manner as in the reaction of the compound (7) and the compound (8) in Reaction Scheme-5.

The subsequent de-acetal reaction of the compound (17) is carried out in an appropriate inert solvent in the presence of an acidic compound. The inert solvent includes, for example, ethers such as dimethyl ether, THF, dioxane, etc.; lower alcohols such as methanol, ethanol, etc.; halogenated hydrocarbons such as dichloromethane, dichloroethane, chloroform, etc.; aromatic hydrocarbons such as benzene, toluene, xylene, etc.; aliphatic hydrocarbons such as hexane, heptane, octane, etc.; acetic acid esters such as methyl acetate, ethyl acetate, etc.; aprotic polar solvents such as DMF, DMSO, HMPA, etc.; carbon disulfide; water; or a mixture of water and the above organic solvents. The acidic compound includes, for example, inorganic acids such as hydrochloric acid, nitric acid, sulfuric acid, etc.; Lewis acids such as anhydrous aluminum chloride, stannic chloride, titanium tetrachloride, boron trichloride, zinc chloride, etc.; organic acids such as trichloroacetic acid, trifluoroacetic acid, methanesulfonic acid, acetic acid, etc.; acid type ion exchange resins; and the like.

The acidic compound is usually used in an amount of about 1 to 100 moles, preferably about 1 to 10 moles, to 1 mole of the compound (17). The reaction temperature is in the range of about −30° to 150° C., preferably about −10° to 100° C., and the reaction period is in the range of about 20 minutes to about 24 hours, preferably about 30 minutes to about 12 hours.

[Reaction Scheme-12]

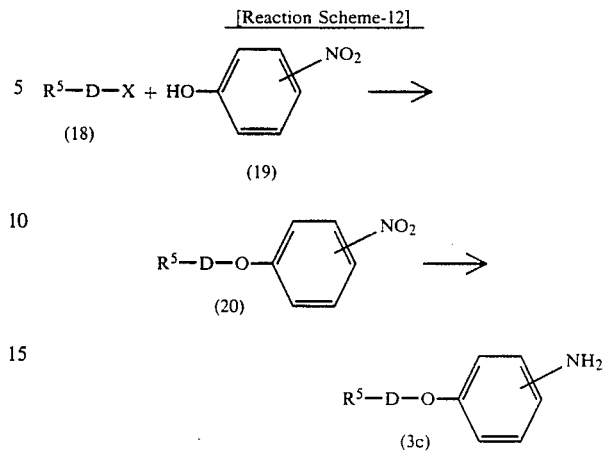

wherein $R^5$, D and X are as defined above.

According to the above Reaction Scheme-12, the compound of the formula (18) and the compound of the formula (19) are reacted and the resulting compound (20) is reduced to give the compound of the formula (3c).

The reaction of the compound (18) and the compound (19) is carried out in the same manner as in the reaction of the compound (2) and the compound (3) in Reaction Scheme-1.

Besides, the reduction of the compound (20) obtained above is carried out in the same manner as in each process in Reaction Scheme-2 or by using stannous chloride etc. as a reducing catalyst under the same conditions.

[Reaction Scheme-13]

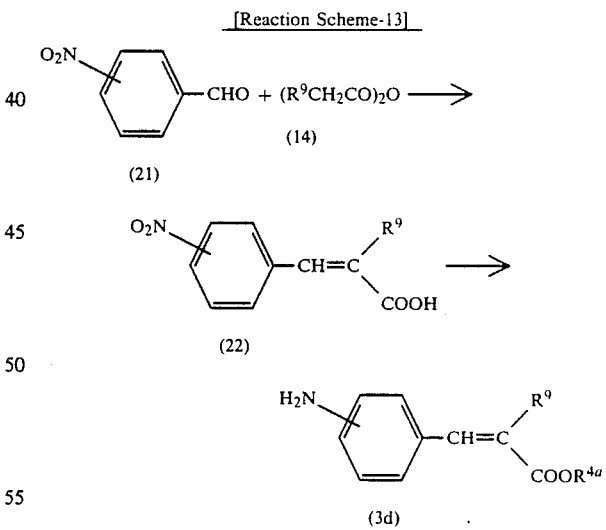

wherein $R^9$ and $R^{4a}$ are as defined above.

According to the above Reaction Scheme-13, the compound of the formula (21) and the compound of the formula (14) are reacted and the resulting compound of the formula (22) is esterified and then reduced to give the compound of the formula (3d).

The reaction of the compound (21) and the compound (14) is carried out in the same manner as in the reaction shown in Reaction Scheme-10. Besides, the esterification of the compound of the formula (22) can be carried out in usual manner, and the subsequent reduction can be carried out by a conventional reduction as in Reaction Scheme-9.

[Reaction Scheme-14]

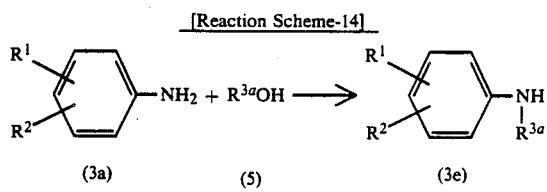

wherein $R^1$, $R^2$ and $R^{3a}$ are as defined above.

According to the above Reaction Scheme-14, the compound of the formula (3a) and the compound of the formula (5) are reacted to give the compound of the formula (3e).

This reaction can be carried out under the same conditions as shown in Reaction Scheme-3.

[Reaction Scheme-15]

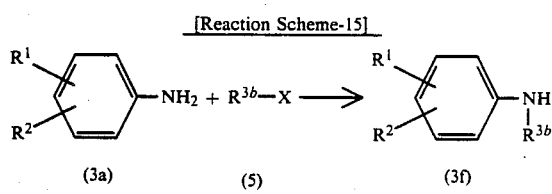

wherein $R^1$, $R^2$, $R^{3b}$ and X are as defined above.

According to the above Reaction Scheme-15, the compound of the formula (3a) and the compound of the formula (6) are reacted to give the compound of the formula (3f).

This reaction can be carried out under the same conditions as shown in Reaction Scheme-4.

[Reaction Scheme-16]

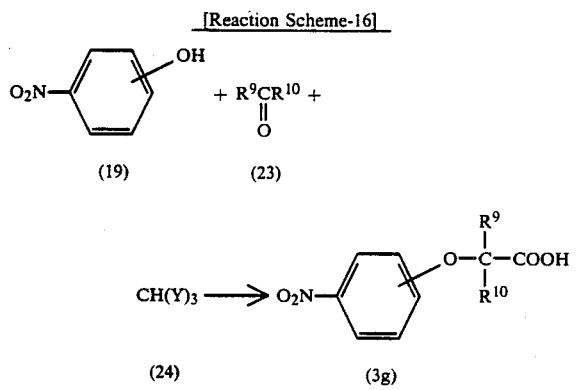

wherein $R^9$, $R^{10}$ and Y are as defined above.

According to the above Reaction Scheme-16, the compound of the formula (19) and the compound of the formula (23) are reacted in the presence of a basic compound, followed by reacting with rhe compound of the formula (24) to give the compound of the formula (3g).

In the reaction of the compound (19) and the compound (23), the basic compound used therein includes inorganic basic compounds such as alkali metal hydroxides (e.g. sodium hydroxide, potassium hydroxide, etc.), alkali metals (e.g. sodium, potassium, etc.), alkali metal hydrides (e.g. sodium hydride, etc.), and the like. The basic compound is usually used in an amount of about 3 to 15 moles, preferably about 4 to 7 moles, to 1 mole of the compound (19). Besides, the compound (23) is usually used in an amount of about 2 to 100 moles, preferably about 5 to 15 moles, to 1 mole of the compound (19).

The amount of the compound (24) to be added to the reaction mixture is usually in the range of about 1 to 10 moles, preferably about 1 to 1.5 mole, to 1 mole of the compound (19). This reaction is carried out at about 10° to 180° C., preferably about 50° to 120° C., for about 15 minutes to about 24 hours, preferably about 30 minutes to about 8 hours.

Among the phenylcarboxylic acid derivatives of the formula (1) of this invention, the compounds having a basic group can easily be converted into acid addition salts thereof by treating with a pharmaceutically acceptable acid. The acid includes, for example, inorganic acids such as hyrochloric acid, sulfuric acid, phosphoric acid, hydrobromic acid, etc., and organic acids such as oxalic acid, maleic acid, fumaric acid, malic acid, tartaric acid, citric acid, benzoic acid, acetic acid, p-toluenesulfonic acid, ethanesulfonic acid, etc.

Besides, among the phenylcarboxylic acid derivatives of this invention, the compounds having an acidic group can easily be converted into salts by treating with a pharmaceutically acceptable basic compound. The basic compound includes, for example, metal hydroxides such as sodium hydroxide, potassium hydroxide, calcium hydroxide, etc., alkali metal carbonates or hydrogen carbonates such as sodium carbonate, potassium hydrogen carbonate, sodium hydrogen carbonate, etc.

The compounds of this invention thus obtained can easily be isolated and purified by conventional isolation methods. The isolation methods are, for example, extraction with a solvent, dilution method, recrystallization method, column chromatography, preparative thin layer chromatography, and the like.

The compounds of the formula (1) of this invention may be present in the form of optical isomers, and hence, this invention includes also these isomers. These isomers can easily be resoluted by conventional resolution methods, for example, by using an optical resoluting agent.

The derivatives and their salts of this invention are used in the form of a conventional pharmaceutical preparation. The preparation is prepared by using conventional dilutents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), ointments, and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium salts, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carries into hard gelatin capsules or soft gelatin capsules in a usual manner. In the preparation of injections, the solutions, emulsions or suspensions are sterilized and are preferably made isotonic with the blood. In the preparation of these forms, there are used diluents such as water, aqueous lactic acid solution, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with solubilizers, buffers, anesthetizing agents. Besides, the pharmaceutical preparations may optionally be incorporated with coloring agents, preservatives, perfumes, flavors, sweeting agents, and other medicaments. In the preparations of paste, cream and gel, there may be used diluents such as white vaseline, paraffin, glycerin, cellulose derivatives, polyethylene glycol, silicone, bentonite, and the like.

The amount of the compounds of the formula (1) or their salts of this invention (active ingredient) to be incorporated into the pharmaceutical preparations is not specified but may be selected from a broad range, but is preferably in the range of 1 to 70 % by weight.

The above pharmaceutical preparations may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneosly administered alone or together with a conventional auxiliary liquid (e.g. glucose, amino acid solutions), and further are optionally administered alone in intramuscular, intracutaneous, subcutaneous, or intraperitoneal route. Suppositories are administered in intrarectal route.

The dosage of the above pharmaceutical preparations may be selected in accordance with the usage, ages, sexes and other conditions of the patients, the degree of severity of the diseases, and the like, but is usually in the range of about 0.5 to 100 mg, preferably about 2 to 20 mg, of the active compound of this invention per 1 kg of body weight of the patient per day. The preparation may be administered by dividing into 2 to 4 times per day.

BEST MODE FOR PRACTISING THE INVENTION

This invention is illustrated by the following Reference Examples as to the preparation of the starting compounds to be used for the preparation of the compounds of this invention, Examples as to the preparation of the compounds of this invention, and further, the pharmacological experiments of the compounds of this invention.

REFERENCE EXAMPLE 1 p-Methyl hydroxybenzoate (40 g) and potassium carbonate (54.5 g) in N,N-dimethylformaldehyde (200 ml) were heated with stirring at 100° C. for 1 hour, cooled to 40° C., and then, after adding 1-bromo-3-chloropropane (28.5 ml), the mixture was reacted at 60° C. for 2 hours. After cooling the reaction mixture, water and ethyl acetate were added thereto, and the mixture was separated into layers. The organic layer was washed with water 3 times, concentrated under reduced pressure. To the oily product thus obtained, a small amount of ethyl acetate and n-hexane were added. After the mixture was allowed to stand, the precipitated crystal was collected by filtration and the filtrate was again concentrated under reduced pressure to give the crystal of methy 4-(3-chloropropoxy)benzoate (56.92 g). mp. 52°–55° C.

REFERENCE EXAMPLE 2 p-Methyl hydroxybenzoate (10 g), bromoacetoaldehyde diethylacetal (15.9 ml), and potassium carbonate (16.0 g) in N,N-dimethylformamide (50 ml) were heated with stirring at 100° C. for 24 hours, and cooled to 4° C. To the mixture were added water and ethyl acetate, and the mixture was separated into layers and the organic layer was washed with water 2 times. After concentrated under reduced pressure, it was subjected to column chromatography on silica gel and eluted benzoate (15.31 g).

NMR (DMSO-$d_6$) δppm: 7.90 (d, J=9.0 Hz, 2H), 7.06 (d, J=9.0 Hz, 2H), 4.82 (t, J=5.3 Hz, 1H), 4.04 (d, J=5.3 Hz, 2H), 3.81 (s, 3H), 3.77–3.49 (m, 4H), 1.14 (t, J=7.0 Hz, 6H).

REFERENCE EXAMPLE 3

Methyl 4-(2,2-diethoxyethoxy)benzoate (36.29 g) was dissolved in dioxane (100 ml), added thereto 2N sulfuric acid (200 ml), and the mixture was heated with stirring at 70° C. for 6 hours. After concentrated under reduced pressure to about half volume, it was diluted with water in two fold, and concentrated again under reduced pressure. The precipitate was collected by filtration, and washed successively with aqueous sodium hydrogencarbonate solution and water to give methyl 4-formylmethoxybenzoate (24.39 g). mp. 58°–60° C.

REFERENCE EXAMPLE 4 p-Chlorophenol (7 g), p-nitrobromobenzene (11.0 g) and potassium carbonate (9.02 g) in dimethylsufoxide (35 ml) were heated with stirring at 120° C. for 24 hours and cooled, and the mixture was poured into water. The resulting precipitate was collected by filtration and washed with water. The resultant was heated in a mixed solvent of methanol/water [4:1,(v/v)], and allowed to cool. The resulting product was collected by filtration to give 4-(4-chlorophenoxy)nitrobenzene (12.92 g).

Further, the product was suspended in ethanol (20 ml), and thereto was added conc. hydrochloric acid (45 ml), and further added dropwise a solution of tin dichloride monohydrate (38.55 g) in ethanol (40 ml) over a period of 2 hours with stirring and keeping the temperature of the reaction mixture below 30° C. After reacting at room temperature for 19 hours, tin dichloride monohydrate (43.18 g) (in solid form) was added in portions, and the mixture was further stirred at room temperature for 24 hours. The reaction mixture was concentrated under reduced pressure, and after adding water, it was again concentrated under reduced pressure. The resulting precipitate was collected by filtration, washed with water, and further washed successively with 1N hydrochloric acid, water, 1N aqueous sodium hydroxide solution and water to give 4-(4-chlorophenoxy)aniline (9.16 g). mp. 97°-98° C.

REFERENCE EXAMPLE 5

N,N-dimethylformamide(DMF) (70 ml) and anhydrous potassium carbonate (16 g) were added to p-methyl hydroxybenzoate (17.6 g) and the mixture was stirred at 90°-100° C. for 1 hour. After the reaction mixture was allowed to cool to 50° C., 1,4-dibromobutane (25 g) was added thereto, and the mixture was stirred at 50°-60° C. for 40 minutes. After the reaction mixture was cooled with ice, water (200 ml) and isopropyl ether (150 ml) were added thereto and the mixture was stirred for 10 minutes, and filtered. The filtrate was washed with water 3 times, dried over anhydrous magnesium sulfate, and concentrated under reduced pressure to give methyl 4-(4-bromobutoxy)benzoate (22 g).

NMR (CDCl$_3$) δppm: 7.98 (d, J=8.79 Hz, 2H), 6.89 (d, J=9.01 Hz, 2H), 4.04 (t, J=5.72 Hz, 2H), 3.88 (s, 3H), 3.50-3.41 (m, 2H), 2.09-1.96 (m, 4H).

REFERENCE EXAMPLE 6

A mixture of 4-hydroxybenzaldehyde (60 g), sodium propionate (104 g) and propionic anhydride (190 ml) was stirred at 135°-140° C. for 40 hours. After the mixture was allowed to cool, water (600 ml) was added thereto, and stirred under ice cooling for 2-3 hours. The precipitate was collected by filtration, and washed well with water. Sodium hydroxide (60 g) was completely dissolved in water (800 ml) with stirring under ice cooling, and thereto was added the above-mentioned precipitate, and the mixture was stirred at the same temperature for 30 minutes. The insoluble materials were filtered off, and the filtrate was acidified with 5N hydrochloric acid under ice cooling. The resulting precipitate was collected by filtration, washed well with water to give 4-hydroxy-α-methylcinnamic acid (66 g). mp. 204°-205° C.

REFERENCE EXAMPLE 7

To 4-hydroxy-α-methylcinnamic acid (55 g), absolute methanol (400 ml) and conc. sulfuric acid (10 ml) were added and refluxed for 12 hours. After the reaction mixture was allowed to cool, it was concentrated under reduced pressure. To the residue was added water (300 ml), and the mixture was neutralized with sodium hydrogen carbonate, and the resulting precipitate was collected by filtration, washed with water, and recrystallized from ethyl acetate/nhexane to give methyl 4-hydroxy-α-methylcinnamate (53 g). mp. 103°-104° C.

REFERENCE EXAMPLE 8

Methyl 4-hydroxy-α-methylcinnamate (16.3 g), DMF (50 ml) and anhydrous potassium carbonate (11.7 g) were mixed, and stirred at 90° C. for 1 hour. The reaction solution was allowed to cool to 50° C., added 1-bromo-3-chloropropane (8.4 ml) thereto, and the mixture was stirred at the same temperature for 1 hour. To the reaction mixture was added water (200 ml), and the mixture was extracted with ether (150 ml), washed with water (150 ml) 2 times, and then, dried over anhydrous magnesium sulfate. The ether layer was concentrated urder reduced pressure to give methyl 4-(3-chloropropoxy)-α-methylcinnamate (20 g).

NMR(CDCl$_3$) δppm: 7.63 (s, 1H), 7.37 (d, J=8.79 Hz, 2H), 6.91 (d, J=8.79 Hz, 2H), 4.14 (t, J=5.93 Hz, 2H), 3.80 (s, 3H), 3.74 (t, J=6.15 Hz, 2H), 2.37-2.10 (m, 2H), 2.13 (d, J=1.32 Hz, 3H).

REFERENCE EXAMPLE 9

The following compounds were obtained in the same manner as Reference Example 2.

4-(3-Phthalimidopropoxy)nitrobenzene, mp. 186°-188° C.

4-[2-(N-Morpholino)ethoxy]nitrobenzene, mp. 88°-89° C.

REFERENCE EXAMPLE 10

4-Nitro-α-methylcinnamic acid was obtained in the same manner as Reference Example 6. mp. 202°-205° C.

REFERENCE EXAMPLE 11

Ethyl 4-nitro-α-methylcinnamate was obtained in the same manner as Reference Example 7. mp. 78°-79° C.

REFERENCE EXAMPLE 12

Methyl 4-(3-chloropropoxy)cinnamate was obtained in the same manner as Reference Example 8. mp. 58°-59° C.

REFERENCE EXAMPLE 13

A mixture of 4-isopropylphenol (16.3 g), 4-chloronitrobenzene (15.8 g), dimethylsulfoxide (150 ml) and potassium hydroxide (5.6 g) was stirred at 90° C. for 48 hours. The reaction solution was poured into ice-water (500 ml), and extracted with ethyl acetate (250 ml), washed (3 times) with water, and d ried over anhydrous magnesium sulfate. The solvent was concentrated under reduced pressure to give 4-(4-isopropylphenoxy)nitrobenzene (29.6 g). Further, it was dissolved in ethanol (300 ml), and thereto was added 5 % palladium/carbon (2.9 g) and the mixture was subjected to catalytic reduction at room temperature for 18 hours. The catalyst was filtered off and the filtrate was concentrated under reduced pressure to give 4-(4-isopropylphenoxy)aniline (24.6 g).

NMR(CDCl$_3$) δppm: 7.24-6.67 (m, 8H), 4.45 (br, 2H), 2.95-2.79 (m, 1H), 1.23 (d, J=6.82 Hz,6H).

REFERENCE EXAMPLE 14

Ethyl 4-nitro-α-methylcinnamate (11 g) was dissolved in glacial acetic acid (150 ml), and stirred at room temperature. Then, zinc powder (12 g) was added to the above-mentioned solution over a period of about 1 hour. The mixture was stirred at room temperature for 1 day. The insoluble material was removed by filtration and the filtrate was concentrated under reduced pressure. The residue was dissolved in ethyl acetate, washed successively with water, saturated aqueous sodium hydrogen carbonate solution and water, and dried over anhydrous magnesium sulfate. The solvent was concentrated under reduced pressure to give ethyl 4-amino-α-methylcinnamate (9 g).

NMR(CDCl$_3$) δppm: 7.59 (br, 1H), 7.27 (d, J=8.35 Hz, 2H), 6.66 (d, J=8.57 Hz, 2H), 4.25 (q, J=7.03 Hz, 2H), 3.81 (br, 2H), 2.13 (d, J=1.32 Hz, 3H), 1.33 (t, J=7.03 Hz, 3H).

REFERENCE EXAMPLE 15

4-Nitrophenol (10 g) was dissolved in acetone (58 ml), and thereto was added sodium hydroxide (16.7 g), the mixture was refluxed with stirring. Chloroform (7.5 ml) was added dropwise to the above-mentioned solution over a period of 20 minutes, and it was refluxed with stirring for 5 hours. After the mixture was allowed to cool, the solvent was concentrated under reduced pressure. Water (100 ml) was added to the resulting residue, acidified with conc. hydrochloric acid, and the mixture was extracted with chloroform (250 ml), washed (3 times) with water. This chloroform solution was extracted with saturated aqueous sodium hydrogen carbonate solution (300 ml), acidified with conc. h.dyrochloric acid, and then, extracted with ethyl acetate, washed with water, and dried over anhydrous magnesium sulfate. The solvent was concentrated under reduced pressure to give 4-nitrophenoxyisobutyric acid (10.7 g). mp. 119°–121° C.

REFERENCE EXAMPLE 16

Ethyl 4-nitrophenoxyisobutyrate was obtained in the same manner as Reference Example 7.

Further, to ethyl 4-nitrophenoxyisobutyrate (12 g) were added ethanol (150 ml) and 5 % palladium/carbon (1 g), the mixture was subjected to catalytic reduction at room temperature overnight. The catalyst was filtered off, and the filtrate was concentrated under reduced pressure to give ethyl 4-aminophenoxyisobutyrate (10.5 g).

NMR(CDCl$_3$) δppm: 6.76 (d, J=9.01 Hz, 2H), 6.61 (d, J=9.01 Hz, 2H), 4.22 (q, J=7.03 Hz, 2H), 4.10 (br, 2H), 1.51 (s, 6H), 1.27 (t, J=7.03 Hz, 3H).

REFERENCE EXAMPLE 17

4-(3-Phthalimidopropoxy)aniline was obtained in the same manner as Reference Example 16. mp. 95–96.

REFERENCE EXAMPLE 18 p-Chloroiodobenzene (14 g), p-chloroaniline (11.23 g), potassium carbonate (12.15 g), and cuprous chloride (1.16 g) were suspended in dimethylsulfoxide (15 ml), and heated with stirring at 180°–190° C. for 3 hours and 40 minutes. After cooling the reaction mixture, ethyl acetate was added thereto, and washed with conc. aqueous ammonia 2 times, and with aqueous sodium chloride solution 3 times, and then, the mixture was concentrated under reduced pressure. The resulting residue was subjected to column chromatography on silica gel and eluted with a mixed solvent of chloroform/n-hexane [1:2 (v/v)] to give 4,4'-dichlorodiphenylamine (4.89 g).

MASS: m/e=237 (M+).

NMR(CDCl$_3$) δppm: 7.19 (d, J=9.0 Hz, 4H), 6.94 (d, J=9.0 Hz, 4H).

REFERENCE EXAMPLE 19 p-Chloroaniline (8 g), methanesulfonic acid 2-benzyloxyethyl ester (12.29 g) and sodium hydrogen carbonate (hereinafter, reffered to as sodium bicarbonate) (8.97 g) were dissolved in dioxane (35 ml), suspended and the mixture was heated with stirring for 24 hours. After concentrated under reduced pressure, water and ethyl acetate were added to the mixture and the mixture was separated into layers. The organic layer was washed with water 2 times, and concentrated again under reduced pressure, and the resulting rsidue was subjected to column chromatography on silica gel, and eluted with chloroform/n-hexane [2:1 (v/v)] to give 4-chloro-N-(2-benzyloxyethyl)aniline (4.63 g).

NMR(CDCl$_3$) δppm: 7.33 (s, 5H), 7.10 (d, J=8.8 Hz, 2H), 6.52 (d, J=8.8 Hz, 2H), 4.54 (s, 2H), 3.69 (t, J=5.3 Hz, 2H), 3.27 (t, J=5.3 Hz, 2H).

EXAMPLE 1

(1) Methyl 4-[3-[N-(4-chlorophenyl)amino]propoxy]benzoate hydrochloride.

p-Chloroaniline (25.5 g), methyl 4-(3-chloropropoxy)benzoate (22.85 g) and sodium bicarbonate (16.8 g) were dissolved and suspended in DMF (130 ml), and heated with stirring at 100° C. for 20 hours. After the reaction mixture was cooled to room temperature, it was poured into water. The resulting precipitant was collected by filtration and washed with water, and heated in 10 % aqueous methanol. After cooled the mixture, the precipitate was collected again by filtration, and washed to give crude crystal. Further, the crude crystal was suspended in methanol, and thereto was added conc. hydrochloric acid (8.7 ml), then, methanol was distilled off under reduced pressure. The resulting residue was crushed well in ethyl acetate, collected by filtration, and washed to give the desired product (22.5 g). mp. 130°–132° C.

(2) Methyl 4-[3-[N-(4-chlorophenyl)amino]propoxy]benzoate.

Methyl 4-[3-[N-(4-chlorophenyl)amino]propoxy]benzoate hydrochloride (9.75 g) was suspended in 1N aqueous sodium hydroxide solution (80 ml), and the mixture was stirred for 2 hours, and collected by filtration, and washed with water to give. the desired product (8.71 g). mp. 111°–112° C.

(3) 4-[3-[N-(4-Chlorophenyl)amino]propoxy]benzoic acid.

Methyl 4-[3-[N-(4-chlorophenyl)amino]propoxy]benzoate hydrochloride (22.5 g) was suspended in methanol (200 ml), and a solution of sodium hydroxide (10.11 g) in water (50 ml) was added thereto, and the mixture was heated with stirring at 60° C. for 14 hours. After cooling, the reaction mixture was neutralized with conc. hydrochloric acid (22.0 ml), and concentrated under reduced pressure. The residue was suspended in water, and collected by filtration to give the desired product (19.1 g). mp. 153°–155° C.

EXAMPLES 2–4

The following compounds of Examples 2–4 were obtained in the same manner as Example 1 using the proper starting materials.

EXAMPLE 2

(1) Methyl 4-[3-[N-(4-fluorophenyl)amino]propoxy]benzoate hydrochloride, mp. 130°–133° C.

(2) 4-[3-[N-(4-Fluorophenyl)amino]propoxy]benzoic acid, mp. 148°–151° C.

EXAMPLE 3

(1) Methyl 4-[3-[N-(4-methoxyphenyl)amino]propoxy]benzoate hydrochloride, mp. 163°–165° C.

(2) 4-[3-[N-(4-Methoxyphenyl)amino]propoxy]benzoic acid hydrochloride, mp. 234°–236° C.

EXAMPLE 4

(1) Methyl 4-[4-[N-(4-chlorophenyl)amino]butoxy]benzoate hydrochloride, mp. 153°–155° C.

(2) 4-[4-[N-(4-Chlorophenyl)amino]butoxy]benzoic acid, mp. 184°–185° C.

EXAMPLE 5

(1) Methyl 4-[5-[N-(4-chlorophenyl)amino]pentyl-1-oxy]benzoate hydrochloride.

Methyl p-hydroxybenzoate (3 g) and potassium carbonate (4.09 g) in DMF (30 ml) were heated with stirring at 100° C. for 1 hour, cooled to 40° C., and after adding 1,5-dibromopentane (2.94 ml) thereto, the mixture was reacted at 60° C. for 2 hours. To this reaction solution were added p-chloroaniline (5.03 g) and sodium bicarbonate (3.32 g), and further the mixture was reacted at 100° C. for 4 hours and 30 minutes, and cooled, poured into water. The resulting gummy product was separated by decantation, then, washed with water several times, and treated with aqueous methanol to give the precipitate. The precipitate was collected by filtration, and washed. After adding a solution of conc. hydrochloric acid (1.2 ml) in methanol, the mixture was dried under reduced pressure. The residue was suspended in ethyl acetate, and collected by filtration to give the desired product (1.71 g). mp. 119°–122° C.

(2) 4-[5-[N-(4-Chlorophenyl)amino]pentyl-1-oxy]benzoic acid.

Methyl 4-[5-[N-(4-chlorophenyl)amino]pentyl-1oxy]benzoate hydrochloride (1.5 g) was suspended in methanol (20 ml), and to the mixture was added a solution of sodium hydroxide (0.63 g) in water (5 ml), then, the mixture was heated with stirring under refluxing for 8 hours. After the reaction mixture was cooled, it was neutralized with conc. hydrochloric acid (1.37 ml). The mixture was concentrated under reduced pressure and the residue was suspended in water, and collected by filtration to give the desired product (1.29 g). mp. 178°–180° C.

EXAMPLE 6

The following compounds were obtained in the same manner as Example 5 using the proper starting materials.

(1) Methyl 4-[6-[N-(4-chlorophenyl)amino]hexyl-1oxy]benzoate hydrochloride, mp. 138°–141° C.

(2) 4-[6-[N-(4-Chlorophenyl)amino]hexyl-1 oxy]benzoic acid, mp. 167°–169° C.

EXAMPLE 7

(1) Methyl 4-[3-[N-(4-tert-butylphenyl) amino]propoxy]benzoate.

p-tert-Butylaniline (3.19 ml), methyl 4-(3-chloropropoxy) benzoate (4.14 g) and sodium bicarbonate (3.38 g) in DMF (10 ml) were heated with stirring at 100° C. for 22 hours, and cooled. Water and ethyl acetate were added thereto and the mixture was separated into layers. The organic layer was washed with water 3 times, then, concentrated under reduced pressure. The resulting residue was subjected to column chromatography on silica gel, and eluted with a mixed solvent of chloroform/methanol [20:1 (v/v)] to give the oily desired product (3.55 g).

NMR(CDCl$_3$) δppm: 7.98 (d, J=9.0 Hz, 2H), 7.20 (d, J=8.4 Hz, 2H), 6.90 (d, J=9.0 Hz, 2H), 6.58 (d, J=8.4 Hz, 2H), 4.13 (t, J=5.9 Hz, 2H), 3.87 (s, 3H), 3.34 (t, J=6.6 Hz, 2H), 2.36–1.97 (m, 2H), 1.27 (s, 9H).

(2) 4-[3-[N-(4-tert-Butylphenyl) amino]propoxy]benzoic acid hydrochloride.

Methyl 4-[3-[N-(4-tert-butylphenyl)amino]propoxy]benzoate (1.67 g) was dissolved in methanol (20 ml), and thereto was added a solution of sodium bydroxide (0.79 g) in water (4 ml), and the mixture was heated with stirring at 60° C. for 26 hours. After neutralized with hydrochloric acid, the reaction solution was concentrated under reduced pressure, and the residue was collected by filtration from water, and washed with water, and it was converted into a salt thereof by adding thereto an equivalent amount of hydrochloric acid in methanol. The solution was dried under reduced pressure, and the resultant was recrystallized from a mixed solvent of methanol and ethyl acetate to give the desired product (0.58 g). mp. 193°–194° C.

EXAMPLE 8

The compounds of Example 8 were obtained in the same manner as Example 7 using the proper starting materials.

(1) Methyl 4-[3-[N-(4-methylphenyl)amino]propoxy]benzoate, mp. 105°–106° C.

(2) 4-[3-[N-(4-Methylphenyl)amino]propoxy]benzoic acid hydrochloride, mp. 237°–239° C.

EXAMPLE 9

(1) Methyl 4-[3-[N-(1,4-benzodioxan-6-yl)amino]propoxy]benzoate.

6-Aminobenzodioxane (2.18 g), methyl 4-(3-chloropropoxy)benzoate (3.0 g) and sodium bicarbonate (4.41 g) in DMF (15 ml) were heated with stirring at 100° C. for 22 hours, and cooled. Water and ethyl acetate were added thereto and the mixture was separated into layers. The organic layer was washed with water 3 times, and then, concentrated under reduced pressure. The residue was subjected to column chromatography on silica gel and eluted with chloroform to give the oily desired product (3.86 g).

NMR(CDCl$_3$) δppm: 7.98 (d, J=9.0 Hz, 2H), 6.95–6.64 (m, 3H), 6.23–6.12 (m, 2H), 4.19 (bs, 4H), 4.12 (t, J=5.9 Hz, 2H), 3.88 (s, 3H), 3.28 (t, J=6.6 Hz, 2H), 2.23–1.95 (m, 2H), (2) 4-[3-[N-(1,4-Benzodioxan-6-yl)amino]propoxy]benzoic acid.

Methyl 4-[3-[N-(1,4-benzodioxan-6-yl)amino]propoxy]benzoate (3.86 g) was dissolved in methanol (40 ml), and thereto was added a solution of sodium hydroxide (1.35 g) in water (10 ml), and the mixture was heated with stirring at 60° C. for 20 hours. The reaction solution was concentrated under reduced pressure, and dissolved in water, then, washed with ether 2 times. The water layer was neutralized with conc. hydrochloric acid, and the resulting precipitate was collected by filtration, washed with cold water to give crude crystal. The crude crystal was dissolved in a mixed solvent of methanol and ethyl acetate, then, concentrated and dried after adding silica gel thereto under reduced pressure. The resulting residue was subjected to column chromatography on silica gel and eluted with a mixed solvent of chloroform/methanol [25:1 (v/v)] to give the desired product (1.76 g). mp. 171°–173° C.

EXAMPLE 10

(1) Methyl 4-[3-[N-(3,4-methylenedioxyphenyl)amino]propoxy]benzoate 3,4-Methylenedioxyaniline (1.80 g), methyl 4-(3chloropropoxy)benzoate (2.0 g) and sodium bicarbonate (1.47 g) in toluene (20 ml) were heated with stirring under refluxing for 29 hours. The reaction solution was concentrated under reduced pressure, and thereto were added water and an equivalent amount of conc. hydrochloric acid, then, the resulting precipitate was collected by filtration. After washed with water, the precipitate was recrystallized from aqueous methanol to give the desired product (2.17 g). mp. 124°-127° C.

(2) 4-[3-[N-(3,4-Methylenedioxyphenyl)amino]propoxy]benzoic acid

Methyl 4-[3-[N-(3,4-methylenedioxyphenyl)amino]propoxy]benzoate (1.5 g) was suspended in methanol (20 ml), and thereto a solution of sodium hydroxide (0.55 g) in water (5 ml) was added, then, the mixture was heated with stirring at 60° C. for 13 hours. After the reaction solution was concentrated under reduced pressure, the residue was washed with ether several times, and further thereto were added water and a neutralization amount of conc. hydrochloric acid. The resulting crystal was collected by filtration to give the desired product (0.99 g). mp. 164°-167° C. (decomposed).

EXAMPLE 11

The compounds of Example 11 were obtained in the same manner as Example 10 using the proper starting material.

(1) Methyl 4-[3-[N-(4-nitrophenyl)amino]propoxy]benzoate, mp. 140°-142° C.

(2) 4-[3-[N-(4-Nitorophenyl)amino]propoxy]benzoic acid, mp. 213°-214° C.

EXAMPLE 12

4-[3-[N-(4-Isopropylphenyl)amino]propoxy]benzoic acid p-Isopropylaniline (1.79 ml), methyl 4-(3-chloropropoxy)benzoate (1.5 g) and sodium bicarbonate (1.10 g) in DMF (5 ml) were heated with stirring at 100° C. for 19 hours, and cooled. Water and ethyl acetate were added thereto and the mixture was separated into layers and the organic layer was washed with water 2 times. After adding an equivalent amount of hydrochloric acid, the organic layer was dried under reduced pressure. The resulting residue was collected by filtration from the ethyl acetate and washed to give the hydrochloride. Further, the hydrochloride was suspended in methanol (20 ml), and a solution of sodium hydroxide (1.05 g) in water (5 ml) was added thereto, and the mixture was heated with stirring at 60° C. for 16 hours. After the reaction solution was concentrated under reduced pressure, the residue was washed with ether several times, and thereto were added water and a neutralization amount of hydrochloric acid. The resulting precipitate was collected by filtration, and recrystallized from aqueous methanol to give the desired product (1.17 g). mp. 188°-194° C. (decomposed)

EXAMPLES 13-16

The following compounds of Examples 13-16 were obtained in the same manner as Example 12 using the proper starting materials.

EXAMPLE 13

4-[3-[N-(3,4-Dichlorophenyl)amino]propoxy]benzoic acid, mp. 160°-161° C.

EXAMPLE 14

4-[3-[N-(4-Cyclohexylphenyl)amino]propoxy]benzoic acid, mp. 157°-161° C.

EXAMPLE 15

4-[3-[N-(4-Chlorophenoxyphenyl)amino]propoxy]benzoic acid, mp. 152°-154° C.

EXAMPLE 16

4-[3-[N-(3-Chloro-4-methylphenyl)amino]propoxy]benzoic acid, mp. 160°-164° C.

EXAMPLE 17

(1) Methyl 4-[2-[N-(4-chlorophenyl)amino]ethoxy]benzoate p-Chloroaniline (0.99 g) and methyl 4-formylmethoxybenzoate (1.5 g) were dissolved in anhydrous methanol (10 ml), and stirred at room temperature for 30 minutes. To the mixture was added sodium cyanoboron hydride (in solid form) (0.24 g) over a period of 30 minutes and further stirred for 30 minutes. After the reaction solution was concentrated under reduced pressure, water and chloroform were added thereto, and the mixture was separated into layers. The organic layer was concentrated under reduced pressure, and subjected to column chromatograpy on silica gel and eluted with chloroform to give the desired product (0.42 g).

NMR(CDCl$_3$) δppm: 7.99 (d, J=9.0 Hz, 2H), 7.14 (d, J=9.0 Hz, 2H), 6.96 (d, J=9.0 Hz, 2H), 6.59 (d, J=9.0 Hz, 2H), 4.20 (t, J=5.3 Hz, 2H), 3.88 (s, 3H), 3.52 (t, J=5.3 Hz, 2H).

(2) 4-[2-[N-(4-Chlorophenyl)amino]ethoxy]benzoic acid hydrochloride

Methyl 4-[2-[N-(4-chlorophenyl)amino]ethoxy]benzoate (0.4 g) was suspended in methanol (20 ml), and thereto a solution of sodium hydroxide (0.16 g) in water (5 ml) was added, and the mixture was heated with stirring at 60° C. for 3 hours. The reaction mixture was cooled, and neutralized with hydrochloric acid and concentrated under reduced pressure. After adding water thereto, the resulting residue was crushed, then, collected by filtration to give crude crystal. An equivalent amount of hydrochloric acid was added to the crude crystal in methanol, and the mixture was dried under reduced pressure to give a salt. The salt was suspended in a mixed solvent of methanol and ether, and collected by filtration to give the desired product (0.31 g). mp. 190°-193° C.

EXAMPLE 18

4-[3-[N-[4-(3,4-Ethylenedioxybenzylamino)phenyl]amino]propoxy]benzoic acid (1) Methanol (200 ml) and methyl 4-[3-[N-(4nitrophenyl)amino]propoxy]benzoate (6.9 g) were added to 5 % palladium/carbon (0.7 g) and catalytic reduction was carried out at room temperature overnight. The catalyst was removed by filtration, and the filtrate was concentrated under reduced pressure, then, to the residue was added isopropyl ether. The insoluble product was collected by filtration to give methyl 4-[3-[N-(4-aminophenyl)amino]propoxy]benzoate (5.5 g).

NMR(CDCl$_3$) δppm: 7.98 (d, J=9.01 Hz, 2H), 6.90 (d, J=8.79 Hz, 2H), 6.70-6.48 (m, 4H), 4.12 (t, J=5.93 Hz, 2H), 3.88 (s, 3H), 3.50-3.15 (br, 4H), 2.25-1.95 (m, 2H), (2) To the compound (amino compound) (2.6 g) obtained above, benzene (100 ml), p-roluenesulfonic acid (0.3 g) and 3,4-ethylenedioxybenzaldehyde (1.4 g) were added and the mixture was refluxed overnight using Dean-Stark Apparatus. The reaction mixture was concentrated under reduced pressure, and to the resulting residue were added ethanol (100 ml) and tetrahydrofuran (30 ml), and then, the mixture was stirred at room temperature, and thereto was added sodium borohydride (0.33 g) slowly, then the mixture was stirred at the same temperature overnight. The resulting mixture was concentrated under reduced pressure, and to the resulting residue was added water (100 ml), and it was neutralized with 1N hydrochloric acid. The insoluble product was collected by filtration, and washed with water and ethyl acetate to give methyl 4-[3-[N-[4-(3,4-ethylenedioxybenzylamino) phenyl]amino]propoxy]benzoate (2.1 g). mp. 185°–188° C.

(3) To methyl 4-[3-[N-[4-(3,4-ethylenedioxybenzylamino) phenyl]amino]propoxy]benzoate (2.1 g) were added methanol (100 ml), tetrahydrofuran (20 ml) and 2N sodium hydroxyide (12 ml), and the mixture was stirred at 45°–50° C. overnight. To the reaction mixture was added water (150 ml), then, after the mixture was neutralized with 2N hydrochloric acid, the resulting precipitate was collected by filtration, washed with water and ethanol to give 4-[3-[N-[4-(3,4-ethylenedioxybenzylamino)phenyl]amino]propoxy]benzoic acid (0.4 g). mp. 246°–247° C.

EXAMPLE 19

4-[3-[N-(4-Chlorophenyl)amino]propoxy]-α-methylcinnamic acid (1) Sodium hydrogen carbonate (3.5 g), 4-chloroaniline (10.45 g) and DMF (50 ml) were added to methyl 4-(3-chloropropoxy)-α-methylcinnamate (11 g), and the mixture was stirred at 100° C. overnight. After the reaction mixture was allowed to cool, water (200 ml) was added thereto, and further the mixture was stirred at room temperature for 30 minutes. The insoluble product was collected by filtration, washed well with water, and was added cold methanol (20ml) thereto, and the mixture was stirred. The resulting crystal was collected by filtration to give methyl 4-[3-[N-(4chlorophenyl)amino]propoxy]-α-methylcinnamate (8 g). mp. 62°–64° C.

(2) Methanol (50 ml) and 2N sodium hydroxide (1 ml) were added to the above-mentioned compound (2 g), and the mixture was stirred at 40°–50° C. overnight. The reaction mixture was concentrated under reduced pressure, and to the residue was added water (50 ml), and the mixture was neutralized with 2N hydrochloric acid with stirring under ice cooling. The resulting crystal was collected by filtration, and washed successively with water and ethanol to give 4-[3-[N-(4-chlorophenyl)amino]propoxy]-α-methylcinnamic acid (1.7 g). mp. 188°–193° C.

EXAMPLE 20

(1) Methyl 4-[3-[N-(4-tert-Butylphenyl)-N-(3,4-methylenedioxybenzoyl) amino]propoxy]benzoate Methyl 4-[3-[N-(4-tert-butylphenyl)amino]propoxy]benzoate (1.80 g) and triethylamine (3.65 ml) were dissolved in THF (40 ml), and cooled with ice, and piperonyl chloride (1.46 g) was added thereto, and the mixture was stirred at room temperature for 16 hours. After the reaction solution was concentrated under reduced pressure, water and ethyl acetate were added thereto and the mixture was separated into layers. The organic layer was washed with water 3 times, and dried under reduced water. The resulting residue was subjected to column chromatography on silica gel and eluted with chloroform to give the desired product (2.01 g).

NMR(CDCl$_3$) δppm: 7.95 (d, J=9.0 Hz, 2H), 7 23 (d, J=8.8 Hz, 2H), 6.98–6.74 (m, 6H), 6.54 (d, J=8.4 Hz, 1H), 5.88 (s, 2H), 4.08 (t, J=6.5 Hz, 4H), 3.87 (s, 3H), 2.31–2.03 (m, 2H), 1.25 (s, 9H).

(2) 4-[3-[N-(4-tert-Butylphenyl) -N-(3,4-methylenedioxybenzoyl)amino]propoxy]benzoic acid Methyl 4-[3-[N-(4-tert-butylphenyl) -N-(3,4methylenedioxybenzoyl)amino]propoxy]benzoate (2.0 g) was dissolved in methanol (40 ml) and thereto was added a solution of sodium hydroxide (0.33 g) in water (10 ml), the mixture was heated with stirring at 60° C. for 23 hours. The reaction solution was cooled, and the solution was adjusted to pH 4–5 with conc. hydrochloric acid. The mixture was diluted with water and the precipitate was collected by filtration and washed with water. The precipitate was recrystallized from ethyl acetate/hexane to give the desired product (1.57 g). mp. 199°–203° C.

EXAMPLES 21–24

The following compounds of Examples 21–24 were obtained in the same manner as Example 20 using the proper starting materials.

EXAMPLE 21

(1) Methyl 4-[3-[N-(4-tert-butylphenyl) -N-(4chlorobenzoyl)amino]propoxy]benzoate NMR(CDCl$_3$) δppm: 7.96 (d, J=9.0 Hz, 2H), 7.26–6.82 (m, 10H), 4.09 (t, J=6.3 Hz, 4H), 3.87 (s, 3H), 2.32–2.02 (m, 2H), 1.25 (s, 9H).

(2) 4-[3-[N-(4-tert-Butylphenyl]-N-(4-chlorobenzoyl)amino]propoxy]benzoic acid, mp. 207°–209° C.

EXAMPLE 22

Methyl 4-[3-[N-(4-tert-butylbenzoyl) -N-(4-chlorophenyl)amino]propoxy]benzoate

NMR (CDCl$_3$) δppm: 7.96 (d, J=9.0 Hz, 2H), 7.24–7.14 (m, 6H), 6.97 (d, J=9.0 Hz, 2H), 6.85 (d, J=9.0 Hz, 2H), 4.09 (t, J=6.3 Hz, 4H), 3.88 (s, 3H), 2.31–2.01 (m, 2H), 1.24 (s, 9H).

(2) 4-[3-[N-(4-tert-Butylbenzoyl) -N-(4-chlorophenyl)amino]propoxy]benzoic acid, mp. 201°–203° C.

EXAMPLE 23

(1) Methyl 4-[3-[N-(4-chlorophenyl) -N-(3,4methylenedioxybenzoyl)amino]propoxy]benzoate NMR (CDCl$_3$) δppm: 7.96 (d, J=9.0 Hz, 2H), 7.21 (d, J=9.0 Hz, 2H), 7.01–6.53 (m, 7H), 5.91 (s, 2H), 4.15–3.99 (m, 4H), 3.88 (s, 3H), 2.31–2.01 (m, 2H).

(2) 4-[3-[N-(4-Chlorophenyl) -N-(3,4-methylenedioxybenzoyl)amino]propoxy]benzoic acid, mp. 182°–184° C.

EXAMPLE 24

(1) Methyl 4-[3-[N-(4-chlorobenzoyl) -N-(4-chlorophenyl)amino]propoxy]benzoate, mp. 119°–120° C.

(2) 4-[3-[N-(4-Chlorobenzoyl) -N-(4-chlorophenyl)amino] propoxy]benzoic acid, mp. 169°–171° C.

EXAMPLE 25

(1) Methyl 4-[3-[N-(4-chlorophenyl]-N-ethylamino]propoxy]benzoate

Methyl 4-[3-[N-(4-chlorophenyl)amino]propoxy]benzoate (1.2 g) and sodium bicarbonate (1.58 g) were dissolved and suspended in DMF (10 ml), and ethyl iodide (1.52 ml) was added thereto. The mixture was heated with stirring at 100° C. for 11 hours, and cooled. Water and ethyl acetate were added thereto and the mixture was separated into layers. The organic layer was washed with water 3 times, and concentrated under reduced pressure to give the oily desired product (1.38 g).

NMR (CDCl$_3$) δppm: 7.99 (d, J=9.0 Hz, 2H), 7.12 (d, J=8.8 Hz, H), 6.91 (d, J=8.8 Hz, 2H), 6.61 (d, J=9.0 Hz, 2H), 4.05 (t, J=5.9 Hz, 2H), 3.88 (s, 3H), 3.54–3.22 (m, 4H), 2.20–1.91 (m, 2H), 1.13 (t, J=7.0 Hz, 3H).

(2) 4-[3-[N-(4-Chlorophenyl) -N-ethylamino]propoxy]benzoic acid

Methyl 4-[3-[N-(4-chlorophenyl)-N-ethylamino]-propoxy]benzoate (1.37 g) was dissolved in methanol (20 ml), and a solution of sodium hydroxide (0.48 ml) in water (5 ml) was added thereto, the mixture was heated with stirring at 60° C. for 13 hours. The reaction mixture was cooled, and was added a neutralization amount of conc. hydrochloric acid thereto, then the mixture was concentrated under reduced pressure. The residue was suspended in water, and collected by filtration, and washed with water to give the desired product (1.20 g). mp. 146°–149° C.

EXAMPLES 26-28

The following compounds of Examples 26-28 were obtained in the same manner as Example 25 using the proper starting materials.

EXAMPLE 26

(1) Methyl 4-[3-[N-(4-chlorophenyl) -N-methylamino]propoxy]benzoate

NMR (CDCl$_3$) δppm: 7.99 (d, J=9.0 Hz, 2H), 7.13 (d, J=9.0 Hz, 2H), 6.90 (d, J=9.0 Hz, 2H), 6.62 (d, J=9.0 Hz, 2H), 4.04 (t, J=5.8 Hz, 2H), 3.88 (s, 3H), 3.52 (t, J=6.6 Hz, 2H), 2.91 (s, 3H), 2.20–1.91 (m, 2H).

(2) 4-[3-[N-(4-Chlorophenyl) -N-methylamino]-propoxy]benzoic acid, mp. 173°–174° C.

EXAMPLE 27

(1) Methyl 4-[3-[N-(4-chlorophenyl) -N-isopropylamino]propoxy]benzoate

NMR (CDCl$_3$) δppm: 7.99 (d, J=9.0 Hz, 2H), 7.16 (d, J=9.0 Hz, 2H), 6.93 (d, J=9.0 Hz, 2H), 6.73 (d, J=9.0 Hz, 2H), 4.12–3.96 (m, 3H), 3.89 (s, 3H), 3.34 (t, J=6.6 Hz, 2H), 2.16–1.87 (m, 2H), 1.16 (d, J=6.6 Hz, 6H).

(2) 4-[3-[N-(4-Chlorophenyl) -N-isopropylamino]-propoxy]benzoic acid, mp. 136°–137° C.

EXAMPLE 28

(1) Methyl 4-[3-[N-(4-chlorophenyl) -N-ethoxycabonylmethylamino]propoxy]benzoate NMR (CDCl$_3$) δppm: 7.99 (d, J=9.0 Hz, 2H), 7.13 (d, J=9.0 Hz, 2H), 6.91 (d, J=9.0 Hz, 2H), 6.57 (d, J=9.0 Hz, 2H), 4.27–4.01 (m, 6H), 3.89 (s, 3H), 3.61 (t, J=6.9 Hz, 2H), 2.26–1.97 (m, 2H), 1.23 (t, J=7.0 Hz, 3H).

(2) 4-[3-[N-Carboxymethyl -N-(4-chlorophenyl-]amino]propoxy]benzoic acid, mp. 153°–155° C. (decomposed).

EXAMPLE 29

(1) Methyl 4-[3-[N-acetyl -N-(4-chlorophenyl)amino]propoxy]benzoate

Methyl 4-[3-[N-(4-chlorophenyl)amino]propoxy]benzoate (1.2 g) was dissolved in pyridine (15 ml), and acetic anhydride (0.71 ml) was added thereto. The mixture was stirred at room temperature for 14 hours and concentrated under reduced pressure. The residue was separated into layers by adding ethyl acetate and diluted hydrochloric acid. The organic layer was washed successively with water, saturated aqueous sodium bicarbonate solution and water, and concentrated under reduced pressure to give the desired product (1.38 g). mp. 68°–69° C.

(2) 4-[3-[N-Acetyl-N-(4-chlorophenyl)amino]propoxy]benzoic acid

Methyl 4-[3-[N-acetyl-N-(4-chlorophenyl)amino]-propoxy]benzoate (1.20 g) was dissolved in methanol (20 ml), and 1N aqueous sodium hydroxide solution (4.99 ml) was added thereto, the mixture was heated with stirring at 60° C. for 27 hours. The reaction mixture was cooled, and the mixture was adjusted to pH 4–5 by adding conc. hydrochloric acid. The mixture was concentrated under reduced pressure and thereto was added water. The precipitate was collected by filtration, and washed with water to give the desired product (1.09 g). mp. 169°–171° C.

EXAMPLE 30

(1) Methyl 4-[3-[N-(4-carboxypropionyl) -N-chlorophenyl)amino]propoxy]benzoate

Methyl 4-[3-[N-(4-chlorophenyl)amino]propoxyl-benzoate (2.4 g) was dissolved in pyridine (25 ml), and succinic anhydride (3.01 g) was added thereto, and the mixture was stirred at 60° C. for 15 hours. To the reaction solution was added water, and concentrated under reduced pressure. Water was added to the residue, then, the precipitate was crushed, collected by filtration, and washed with water to give the desired product (3.17 g). mp. 125°–127° C.

(2) 4-[3-[N-(3-Carboxypropionyl) -N-(4-chlorophenyl)amino]propoxy]benzoic acid

Methyl 4-[3-[N-(3-carboxypropionyl) -N-(4-chlorophenyl)amino]propoxy]benzoate (1.0 g) was dissolved in methanol (20 ml), and 1N aqueous sodium hydroxide solution (5.25 ml) was added thereto, and the mixture was heated with stirring at 60° C. for 24 hours. After the reaction mixture was cooled, the mixture was adjusted to pH 4–5 by adding conc. hydrochloric acid thereto. The mixture was concentrated under reduced pressure, and thereto was added water, then, the precipitate was crushed, collected by filtration, and washed with water to give the desired product (0.97 g). mp. 155°–158° C.

EXAMPLES 31-40

The following cdmpounds of Examples 31–40 were obtained in the same manner as Example 1 using the proper starting materials.

EXAMPLE 31

(1) Methyl 4-[3-[N-(4-chlorophenyl)amino]-2methylenepropoxy]benzoate, mp. 54°–56° C.

(2) 4-[3-[N-(4-Chlorophenyl)amino]-2-methylenepropoxy]benzoic acid, mp. 134°–136° C.

EXAMPLE 32

(1) Methyl 4-[4-[N-(4-chlorophenyl)amino]-2-buten1-yloxy]benzoate hydrochloride, mp. 138°–143° C. (decomposed).

(2) 4-[4-[N-(4-Chlorophenyl)amino]-2-buten-1-yloxy]benzoic acid, mp. 187°–189° C. (decomposed).

EXAMPLE 33

(1) Methyl 4-[3-[N-(4-chlorophenyl)amino]propoxy]-cinnamate hydrochloride, mp. 176°–177° C.

(2) 4-[3-[N-(4-Chlorophenyl)amino]propoxy]cinnamic acid, mp. 174°–180° C. (decomposed)

EXAMPLE 34

(1) Methyl 4-[3-[N-[4-(4-isopropylphenoxy]phenyl-]amino]propoxy]benzoate hydrochloride, mp. 163°–164° C.

(2) 4-[3-[N-[4-(4-Isopropylphenoxy]phenyl]amino]-propoxy]benzoic acid hydrochloride, mp. 239°–240° C.

EXAMPLE 35

(1) Methyl 4-[3-[N-(3-chlorophenyl)amino]propoxy]-benzoate, mp. 105°–106° C.

(2) 4-[3-[N-(3-Chlorophenyl)amino]propoxy]benzoic acid, mp. 215°–218° C.

EXAMPLE 36

(1) Methyl 4-[3-[N-(4-acetylphenyl)amino]propoxy]-benzoate hydrochloride, mp. 158°–160° C.

(2) 4-[3-[N-(4-Acetylphenyl)amino]propoxy]benzoic acid, mp. 197°–198° C.

EXAMPLE 37

(1) Methyl 4-[3-[N-(4-chloro-2-methylphenyl)amino]-propoxybenzoate hydrochloride, mp. 173°–175° C.

(2) 4-[3-[N-(4-Chloro-2-methylphenyl)amino]propoxy]benzoic acid, mp. 189°–191° C.

EXAMPLE 38

(1) Methyl 4-[3-[N-(2,4-dichlorophenyl)amino]-propoxy]benzoate, mp. 92°–93° C.

(2) 4-[3-[N-(2,4-Dichlorophenyl)amino]propoxy]benzoic acid, mp. 168°–170° C.

EXAMPLE 39

(1) Methyl 4-[3-[N-(4-bromophenyl)amino]propoxy]-benzoate hydrochloride, mp. 177°–178° C.

(2) 4-[3-[N-(4-Bromophenyl)amino]propoxy]benzoic acid, mp. 155°–157° C.

EXAMPLE 40

(1) Methyl 4-[3-[N-[4-[2-(N-morpholino)ethoxy]-phenyl]amino]propoxy]benzoate, mp. 95°–96° C.

(2) 4-[3-[N-[4-[2-(N-Morpholino)ethoxy]phenyl]amino]propoxy]benzoic acid dihydrochloride, mp. 210°–215° C.

EXAMPLE 41

The following compound (1) was obtained by catalytic reduction in the same manner as Example 18 (1) using the proper starting material, and further, the following compound (2) was obtained in the same manner as Example 1.

(1) Methyl 3-[4-[3-[N-(4-chlorophenyl)amino]-propoxy]phenyl]propionate hydrochloride, mp. 135°–137° C.

(2) 3-[4-[3-[N-(4-Chlorophenyl)amino]propoxy]-phenyl]propionic acid, mp. 89°–91° C.

EXAMPLE 42

The following compound was obtained in the same manner as Example 7 by using the proper starting material.

(1) Methyl 4-[3-[N-[4-(2,3-epoxypropoxy)phenyl]amino]propoxy]benzoate, mp. 105°–106° C.

EXAMPLE 43

The following compounds were obtained in the same manner as Example 7 by using the proper starting materials.

(1) Methyl 4-[3-[N-(4-isopropoxyphenyl)amino]-propoxy]benzoate

NMR (CDCl$_3$) δppm: 7.98 (d, J=9.01 Hz, 2H), 6.90 (d, J=9.01 Hz, 2H), 6.78 (d, J=9.23 Hz, 2H), 6.56 (d, J=9.23 Hz, 2H), 4.41–4.07 (m, 3H), 3.88 (s, 3H), 3.38–3.23 (m, 2H), 2.25–1.95 (m, 2H), 1.28 (d, J=6.15 Hz, 6H).

(2) 4-[3-[N-(4-Isopropoxyphenyl)amino]propoxy]-benzoic acid hydrochloride

NMR (DMSO-d$_6$) δppm: 10.65 (br, 1H), 7.89 (d, J=8.79 Hz, 2H), 7.20–6.83 (m, 6H), 4.57–4.44 (m, 1H), 4.23–4.10 (m, 2H), 3.39–3.19 (m, 2H), 2.20–2.04 (m, 2H), 1.25 (d, J=5.93 Hz, 6H).

EXAMPLE 44

The following compounds were obtained in the same manner as Example 7 by using the proper starting materials.

(1) Ethyl 4-[N-[3-(4-methoxycarbonylphenoxy)-propyl]amino]phenoxyisobutyrate

NMR (CDCl$_3$) δppm: 7.98 (d, J=9.01 Hz, 2H), 6.90 (d, J=9.01 Hz, 2H), 6.78 (d, J=9.01 Hz, 2H), 6.50 (d, J=9.01 Hz, 2H), 4.34–4.07 (m, 4H), 3.88 (s, 3H), 3.38–3.23 (m, 2H), 2.20–2.02 (m, 2H), 1.50 (s, 6H), 1.28 (t, J=7.04 Hz, 3H).

(2) 4-[N-[3-(4-Carboxyphenoxy)propyl]amino]-phenoxyisobutyric acid, mp. 198°–199° C.

EXAMPLE 45

After catalytic reduction in the same manner as Example 18 (1) using the proper starting material, the following compound was obtained in the same manner as Example 12.

(1) 3-[4-[3-[N-(4-Chlorophenyl)amino]propoxy]-phenyl]-2-methylpropionic acid p-toluenesufonate, mp. 109°–111° C.

EXAMPLE 46

The following compounds were obtained in the same manner as Example 19 by using the proper starting materials.

(1) Methyl 4-[3-[N-(4-benzyloxyphenyl)amino]-propoxy]benzoate, mp. 115°–117° C.

(2) 4-[3-[N-(4-Benzyloxyphenyl)amino]propoxy]benzoic acid.

NMR (DMSO-d$_6$) δppm: 7.85 (d, J=8.57 Hz, 2H), 7.35 (s, 5H), 6.82 (d, J=8.79 Hz, 2H), 6.78 (d, J=8.79 Hz, 2H), 6.52 (d, J=9.0 Hz, 2H), 4.95 (s, 2H), 4.08 (t, J=6.15 Hz, 2H), 3.13 (t, J=6.6 Hz, 2H), 2.05–1.98 (m, 2H).

EXAMPLE 47

4-[3-[N-[4-(3-Aminopropoxy)phenyl]amino]propoxy]benzoic acid (1) The following compound was obtained in the same manner as Example 1 by using the proper starting material.

Methyl 4-[3-[N-[4-(3-phthalimidopropoxy)phenyl]amino]propoxy]benzoate hydrochloride, mp. 180°–181° C.

(2) Further, ethanol (140 ml) and 1N aqueous sodium mentioned compound (4 g), and the mixture was stirred at room temperature for 30 minutes. And hydrazine monohydrate (0.38 g) was added thereto, and the mixture was refluxed for one day. After the mixture was allowed to cool, the resulting crystal was collected by filtration to give the following product (3.1 g).

Methyl 4-[3-[N-[4-(3-aminopropoxy)phenyl]amino]-propoxy]benzoate.

NMR (DMSO-d$_6$) δppm: 7.89 (d, J=10.76 Hz, 2H), 7.02 (d, J=9.01 Hz, 2H), 6.70 (d, J=9.01 Hz, 2H), 6.50 (d, J=9.01 Hz, 2H), 4.84 (br, 2H), 4.20–4.05 (m, 2H), 3.95–3.81 (m, 5H), 3.20–3.05 (m, 2H) 2.80–2.66 (m, 2H), 2.10–1.60 (m, 4H).

(3) Further, to the above-mentioned compound (1 g) was added methanol (50 ml) and 2N aqueous sodium hydroxide solution (7 ml), and the mixture was stirred at 60° C. for 18 hours. After the mixture was allowed to cool, the solvent was distilled off under reduced pressure for concentration. To the residue was added water (20 ml), the mixture was neutralized with 2N hydrochloric acid under ice cooling. The resulting crystal was collected by filtration, washed with water, and recrystallized from methanol to give the desired product (0.5 g).

NMR (DMSO-$d_6$) $\delta$ppm: 8.32 (br, 2H), 7.88 (d, J=8.79 Hz, 2H), 7.00 (d, J=8.79 Hz, 2H), 6.74 (d, J=9.01 Hz, 2H), 6.53 (d, J=9.01 Hz, 2H), 4.22–3.89 (m, 4H), 3.21–2.85 (m, 4H), 2.15–1.85 (m, 4H).

EXAMPLE 48

4-[3-[N-(4-Chlorophenyl)-N-methylamino]propoxy]-cinnamic acid (1) To 4-chloro-N-methylaniline (2.5 g) were added DMF (35 ml), sodium hydrogen carbonate (1.8 g) and methyl 4(3-chloropropoxy)cinnamate (5 g), and the mixture was stirred at 100° C. for 3 days.

After the reaction solution was allowed to cool, water (150 ml) was added thereto, and the mixture was extracted with ethyl acetate (150 ml), washed with water (3 times), then, the solvent was concentrated under reduced pressure. The residue was subjected to column chromatography on silica gel and eluted with chloroform to give oily methyl 4-[3-[N-(4-chlorophenyl) -N-methylamino]propoxy]cinnamate (3.6 g).

NMR (CDCl$_3$) $\delta$ppm: 7.65 (d, J=15.83 Hz, 1H), 7.47 (d, J=6.59 Hz, 2H), 7.12 (d, J=7.91 Hz, 2H), 6.89 (d, J=6.59 Hz, 2H), 6.72 (d, J=7.91 Hz, 2H), 6.30 (d, J=15.83 Hz, 1H), 4.01 (t, J=5.93 Hz, 2H), 3.79 (s, 3H), 3.59–3.44 (m, 2H), 2.91 (s, 3H), 2.12–1 97 (m, 2H).

(2) To the above-mentioned compound (3.6 g) were added methanol (50 ml), THF (20 ml) and 2N aqueous sodium hydroxide solution (12.5 ml), and the mixture was stirred at 60° C. for 18 hours.

After the reaction solution was allowed to cool, it was concentrated under reduced pressure, and to the residue was added water (100 ml). The mixture was acidified with 2N hydrochloric acid with stirring under ice cooling, and the resulting crystal was collected by filtration, washed with water, and washed with methanol to give the desired product (1.3 g). mp. 165°–167° C.

EXAMPLE 49

The following compounds were obtained in the same manner as Example 48 by using the proper starting materials.

(1) Ethyl 4-[N-[3-(4-methoxycarbonylphenoxy)-propyl]amino]-α-methylcinnamate, mp. 91°–92° C.

(2) 4-[N-[3-(4-Carboxyphenoxy)propyl]amino]-α-methylcinnamic acid, mp. 226°–229° C.

EXAMPLES 50–53

The following compounds were obtained in the same manner as Example 25 by using the proper starting materials.

EXAMPLE 50

(1) Methyl 4-[3-[N-(4-chlorophenyl)-N-isobutylamino]propoxy]benzoate

NMR (CDCl$_3$) $\delta$ppm: 7.99 (d, J=9.0 Hz, 2H), 7.12 (d, J=9.0 Hz, 2H), 6.90 (d, J=9.0 Hz, 2H), 6.60 (d, J=900 Hz, 2H), 4.03 (t, J=5.8 Hz, 2H), 3.88 (s, 3H), 3.5 (t, J=7.0 Hz, 2H), 3.05 (d, J=7.3 Hz, 2H), 2.18–1.90 (m, 3H), 0.90 (d, J=6.4 Hz, 6H).

(2) 4-[3-[N-(4-Chlorophenyl) -N-isobutylamino]propoxy]benzoic acid, mp. 123°–125° C .

EXAMPLE 51

(1) Methyl 4-[3-[N-allyl-(4-chlorophenyl)amino]propoxy]benzoate hydrochloride

NMR (CDCl$_3$) $\delta$ppm: 7.91 (d, J=9.0 Hz, 2H), 7.14 (d, J=6.5 Hz, 2H), 7.04 (d, J=6.5 Hz, 2H), 6.68 (d, J=9.0 Hz, 2H), 5.99–5.63 (m, 1H), 5.17–4.99 (m, 2H), 4.11 (t, J=5.9 Hz, 2H), 3.92 (d, J=4.8 Hz, 2H), 3.81 (s, 3H), 3.47 (t, J=7.0 Hz, 2H), 2.14–1 84 (m, 2H).

(2) 4-[3-[N-Allyl-N-(4-chlorophenyl)amino]propoxy]benzoic acid, mp. 131°–132° C.

(1) Methyl 4-[3-[N-(4-chlorophenyl)-N-methallylamino]propoxy]benzoate

NMR (CDCl$_3$) $\delta$ppm: 7.99 (d, J=8.8 Hz, 2H), 7.10 (d, J=9.0 Hz, 2H), 6.90 (d, J=8.8 Hz, 2H), 6.57 (d, J=9.0 Hz, 2H), 4.79 (d, J=8.4 Hz, 2H), 4.06 (t, J=5.8 Hz, 2H), 3.89 (s, 3H), 3.76 (bs, 2H), 3.53 (t, J=7.1 Hz, 2H), 2.22–1.94 (m, 2H), 1.70 (bs, 3H).

(2) 4-[3-[N-(4-Chlorophenyl}-N-methallylamino]propoxy]benzoic acid, mp. 146°–148° C.

EXAMPLE 53

(1) Methyl 4-[3-[N-(4-chlorobenzyl)-N-(4-chlorophenyl)amino]propoxy]benzoate hydrochloride, mp. 111°–115° C.

(2) 4-[3-[N-(4-Chlorobenzyl)-N-(4-chlorophenyl)amino]propoxy]benzoic acid, mp. 164°–166° C.

EXAMPLE 54

(1) Methyl 4-[3-[N-(4-chlorophenyl)-N-cyanomethylamino]propoxy]benzoate

Methyl 4-[3-[N-(4-chlorophenyl)amino]propoxy]benzoate (1.2 g) was dissolved in DMF (10 ml), and under heating with stirring at 90° C., sodium bicarbonate (7.6 g) and chloroacetonitrile (6.63 g) were added thereto in 8–10 portions respectively over a period of 7 days. The reaction mixture was cooled, and water and ethyl acetate were added thereto and the mixture was separated into layers. The organic layer was washed with aqueous sodium chloride solution, and concentrated under reduced pressure. The residue was subjected to column chromatography on silica gel and eluted with chloroform to give the oily desired product (1.00 g).

NMR (CDCl$_3$) $\delta$ppm: 7.99 (d, J=9.0 Hz, 2H), 7.24 (d, J=9.0 Hz, 2H), 6.96–6.75 (m, 4H), 4.13–4.02 (m, 4H), 3.89 (s, 3H), 3.58 (t, J=6.9 Hz, 2H), 2.26–1.99 (m. 2H).

(2) 4-[3-[N-(4-Chlorophenyl)-N-cyanomethylamino]propoxy]benzoic acid

Methyl 4-[3-[N-(4-chloropheny)-N-cyanomethylamino]propoxy]benzoate (0.99 g) was dissolved in dioxane (15 ml), and thereto was added a solution of sodium hydroxide (0.33 g) in water (4 ml), and stirred at room temperature for 20 hours. The reaction mixture was neutralized by adding conc. hydrochloric acid (0.72 ml) thereto, then, the mixture was dried under reduced pressure. The resultant was dissolved in a mixed solvent of ethanol/chloroform, and filtered and dried again under reduced pressure to give a residue.

The residue was dissolved in THF (20 ml), and thereto was added pyridine (0.85 ml), and then, trifluoroacetic anhydride (1.47 ml) was added dropwise to the mixture under ice cooling over a period of 10 minutes, and the mixture was stirred at room temperature for 2 hours. After a small amount of water was added to the reaction mixture, the mixture was concentrated under reduced pressure. The residue was suspended in water, and collected by filtration, and recrystallized from 40 % aqueous methanol to give the desired product (0.81 g). mp. 154°–157° C.

EXAMPLE 55

(1) 3-(4,4′-Dichlorodiphenylamino)propanol

Acrylic acid (9.67 ml) was added to 4,4′-dichlorodiphenylamine (4.80 g), and heated with stirring at 130° C. for 19 hours. The excess acrylic acid was distilled off under reduced pressure, and to the residue was added a solution of sodium hydroxide (8 g) in water (60 ml), and the mixture was treated at 60° C. for 1 hour. After the reaction mixture was cooled, it was diluted with water, washed with ether several times. After a neutralization amount of conc. hydrochloric acid was added thereto, the mixture was extracted with ethyl acetate, dried over anhydrous magnesium sulfate, and concentrated under reduced pressure to give an oily product (5.81 g).

Lithium aluminum hydride (2.13 g) was suspended in THF (120 ml) under ice cooling, and thereto a solution of the above-mentioned oily product in THF (about 20 ml) was added gradually, then, the mixture was stirred at room temperature for 19 hours. To the reaction mixture were added ethyl acetate and a small amount of 1N aqueous sodium hydroxide solution to decompose the excess reducing agent. Then, the mixture was filtered, and concentrated under reduced pressure to give the oily desired product (3.24 g).

NMR (CDCl$_3$) δppm: 7.19 (d, J=9.0 Hz, 4H), 6.94 (d, J=9.0 Hz, 4H), 3.88–3.62 (m, 4H), 2.04–1.42 (m, 2H).

(2) Methyl 4-[3-(4,4′-dichlorodiphenylamino)propoxy]benzoate 3-(4,4′-Dichlorodiphenylamino)propanol (5.44 g) and triethylamine (7.63 ml) were dissolved in methylene chloride (60 ml), and after the mixture was cooled with ice, methanesulfonyl chloride (1.99 ml) was added thereto, then, the mixture was stirred at room temperature for 3 hours, and concentrated under reduced pressure. Water and ethyl acetate were added to the residue and the mixture was separated into layers. The organic layer was washed with water 2 times, and dried over anhydrous magnesium sulfate and concentrated under reduced pressure to give oily mesylate compound (6.19 g).

This mesylate compound was dissolved in DMF (100 ml), and thereto methyl p-hydroxybenzoate (2.52 g) and potassium carbonate (6.85 g) were added, and the mixture was heated with stirring at 90° C. for 17 hours. After the reaction mixture was cooled, water and ethyl acetate were added thereto and the mixture was separated into layers. The organic layer was washed with water 3 times, and concentrated nder reduced pressure. The resulting residue was subjected to column chromatography on silica gel and eluted with chloroform to give the oily desired product (6.09 g).

NMR (CDCl$_3$) δppm: 7.99 (d, J=9.0 Hz, 2H), 7.19 (d, J=9.0 Hz, 4H), 6.95–6.83 (m, 6H), 4.12–3.82 (m, 7H), 2.26–1.96 (m, 2H).

(3) 4-[3-(4,4′-Dichlorodiphenylamino)propoxy]benzoic acid

Methyl 4-[3-(4,4′-dichlorodiphenylamino)propoxy]benzoate (6.08 g) was dissolved in methanol (100 ml), and thereto was added a solution of sodium hydroxide (1.70 g) in water (20 ml), and the mixture was heated with stirring at 60° C. for 14 hours.

After the reaction mixture was cooled, conc. hydrochloric acid (3.70 ml) was added thereto, then, the mixture was concentrated under reduced pressure. The residue was crushed after adding water, and then collected by filtration and recrystallized from a mixed solvent of ethyl acetate/n-hexane [2:5 (v/v)] to give the desired product (3.93 g). mp. 118°–120° C.

EXAMPLES 56–57

The following compounds were obtained in the same manner as Example 55 by using the proper starting materials.

EXAMPLE 56

(1) 3-Diphenylaminopropanol

NMR (CDCl$_3$) δppm: 7.34–6.92 (m, 10H), 3.93–3.66 (m, 4H), 2.04–1.67 (m, 2H).

(2) Methyl 4-(3-diphenylaminopropoxy)benzoate

NMR (CDCl$_3$) δppm: 7.97 (d, J=9.0 Hz, 2H), 7.34 m, 12H), 4.14–3.88 (m, 7H), 2.30–2.01 (m, 2H).

(3) 4-(3-Diphenylaminopropoxy)benzoic acid, mp. 196°–199° C.

EXAMPLE 57

(1) 3-[N-(2-Benzyloxyethyl)-N-(4-chlorophenyl)amino]propanol

NMR (CDCl$_3$) δppm: 7.31 (s, 5H), 7.13 (d, J=9.0 Hz, 2H), 6.63 (d, J=9.0 Hz, 2H), 4.51 (s, 2H), 3.74–3.36 (m, 8H), 1.95–1.65 (m, 2H).

(2) Methyl 4-[3-[N-(2-benzyloxyethyl)-N-(4-chlorophenyl)amino]propoxy]benzoate

NMR (CDCl$_3$) δppm: 7.98 (d, J=8.8 Hz, 2H), 7.29 (bs, 5H), 7.12 (d, J=9.0 Hz, 2H), 6.88 (d, J=8.8 Hz, 2H), 6.62 (d, J=9.0 Hz, 2H), 4.48 (s, 2H), 4.02 (t, J=5.8 Hz, 2H), 3.88 (s, 3H), 3.61–3.47 (m, 6H), 2.21–1.91 (m, 2H).

(3) 4-[3-[N-(2-Benzyloxyethyl)-N-(4-chlorophenyl)amino]propoxy]benzoic acid, mp. 76°–81° C.

EXAMPLE 58

4-[3-[N-(4-Chlorophenyl)-N-(2-hydroxyethyl)amino]propoxy]benzoic acid

4-[3-[N-(2-Benzyloxyethyl)-N-(4-chlorophenyl)amino]propoxy]benzoic acid (3.5 g) was dissolved in a mixed solvent of ethanol (60 ml) and ethyl acetate (15 ml), and thereto were added conc. hydrochloric acid (0.7 ml) and 10 % palladium/carbon (0.35 g), and the mixture was stirred under hydrogen and atmospheric pressure at room temperature for 27 hours. The reaction mixture was diluted with water, filtered, and neutralized with 1N aqueous sodium hydroxide solution, and then, the mixture was concentrated under reduced pressure. The residue was washed with water, and crystallized from about 50 % aqueous methanol and collected by filtration. The resultant was further recrystallized from a mixed solvent of ethyl acetate/n-hexane [1:10 (v/v)] to give the desired product (1.20 g). mp. 120°–122° C.

EXAMPLE 59

(1) Methyl 4-[3-[N-(2-carboxyethyl)-N-(4-chlorophenyl)amino]propoxy]benzoate

Methyl 4-[3-[N-[4-chlorophenyl)amino]propoxy]benzoate (2.0 g) was dissolved in toluene (6 ml), and thereto was added acrylic acid (2.24 ml), and the mixture was heated with stirring at 100° C. for 24 hours. The reaction mixture was diluted with ethyl acetate, and washed successively with aqueous sodium bicarbonate solution 2 times and water once, and it was concentrated under reduced pressure. The residue was subjected to column chromatography on silica gel and eluted with a mixed solvent of chloroform/methanol [60:1 (v/v)] to give the oily desired product (1.64 g).

NMR (CDCl$_3$) δppm: 7.98 (d, J=8.8 Hz, 2H), 7.15 (d, J=9.2 Hz, 2H), 6.90 (d, J=8.8 Hz, 2H), 6.66 (d, J=9.2 Hz, 2H), 4.03 (t, J=5.8 Hz, 2H), 3.88 (s, 3H), 3.70–3.42 (m, 4H), 2.60 (t, J=7.0 Hz, 2H), 2.20–1.90 (m, 2H).

(2) 4-[3-[N-(2-Carboxyethyl)-N-(4-chlorophenyl)amino]propoxy]benzoic acid

Methyl 4-[3-[N-(2-carboxyethyl)-N-(4-chlorophenyl)amino]propoxy]benzoate (1.37 g) was dissolved in methanol (20 ml) and thereto was added a solution of sodium hyroxide (0.42 g) in water (4 ml), and the mixture was heated with stirring at 60° C. for 23 hours. After the reaction mixture was cooled, a neutralizing amount of conc. hydrochloric acid was added thereto, then, concentrated under reduced pressure. The residue was allowed to stand in water (pH; about 4.5) and the resulting crystal was collected by filtration, washed with water, and recrystallized from about 30 % aqueous methanol to give the desired product (0.87 g). mp. 132°–133° C.

EXAMPLE 60

(1) Methyl 4-[3-[N-carbamoyl-N-(4-chlorophenyl)amino]propoxy]benzoate

Methyl 4-[3-[N-(4-chlorophenyl)amino]propoxy]benzoate (2.5 g) and sodium cyanate (1.02 g) were dissolved and suspended in benzene (7.5 g), and to the mixture was added dropwise trifuluoroacetic acid (1.19 g) under heating with stirring at 40° C. Three hours later, the reaction solution was concentrated under reduced pressure, and water was added to the residue. The resulting precipitate was crushed, and collected by filtration to give the desired product (2.82 g). mp. 141°–142° C.

(2) 4-[3-[N-Carbamoyl-N-(4-chlorophenyl)amino]propoxy]benzoic acid

Methyl 4-[3-[N-carbamoyl-N-(4-chlorophenyl)amino]propoxy]benzoate (1.5 g) was dissolved in dioxane (30 ml), and thereto was added a solution of sodium hydroxide (0.33 g) in water (6 ml), and the mixture was stirred at room temperature for 22 hours. The reaction mixture was neutralized with conc. hydrochloric acid (0.7 ml), and the mixrure was concentrated under reduced pressure. The residue was crushed in aqueous methanol, and collected by filtration to give the desired product (1.27 g). mp. 172°–174° C.

EXAMPLE 61

(1) Methyl 4-[3-[N-[3-(4-chlorophenylcarbamoyl)propionyl]-N-(4-chlorophenyl)amino]propoxy]benzoate Methyl 4-[3-[N-(3-carboxypropionyl)-N-(4-chlorophenyl)amino]propoxy]benzoate (1.6 g), p-chloroaniline (0.54 g), DCC (0.87 g) and 4-dimethylaminopyridine (47 mg) were dissolved in methylene chloride (40 ml), and the mixture was stirred at room temperature for 52 hours, and concentrated under reduced pressure. The residue was dissolved in a small amount of DMF, and filtered. To this filtrate were added water and ethyl acetate and it was separated into layers. The organic layer was washed with water 3 times and concentrated under reduced pressure. The oily product thus obtained was subjected to column chromatography on silica gel and eluted with a mixed solvent of chloroform/methanol [30:1 (v/v)], and then concentrated under reduced pressure. The residue was crushed in aqueous methanol and collected by filtration to give the subject product (1.70 g). mp. 128°–130° C.

(2) 4-[3-[N-[3-(4-Chlorophenylcarbamoyl)propionyl]-N-(4-chlorophenyl)amino]propoxy]benzoic acid Methyl 4-[3-[N-[3-(4-chlorophenylcarbamoyl)propionyl]-N-(4-chlorophenyl)amino]propoxy]benzoate (1.50 g) was dissolved in methanol (20 ml), and thereto was added 1N aqueous sodium hyroxide solution (4.83 ml), and the mixture was heated with stirring at 60° C. for 42 hours. After the reaction mixture was cooled, a neutralizing amount of conc. hydrochloric acid was added thereto, and the mixture was concentrated under reduced pressure. The resultant was suspended in 10 % aqueous methanol, and collected by filtration to give the desired product (1.04 g). mp. 197°–201° C.

EXAMPLE 62

The following compounds were obtained in the same manner as Example 61 by using the proper starting materials.

(1) Methyl 4-[3-[N-(4-chlorophenyl)-N-[2-(4-chlorophenylcarbamoyl)ethyl]amino]propoxy]benzoate NMR (CDCl$_3$) δppm: 7.96 (d, J=9.0 Hz, 2H), 7.33–7.12 (m, 6H), 6.86 (d, J=8.8 Hz, 2H), 6.71 (d, J=9.0 Hz, 2H), 4.01 (t, J=5.9 Hz, 2H), 3.88 (s, 3H), 3.69 (t, J=5.9 Hz, 2H), 3.50 (t, J=5.9 Hz, 2H), 2.57 (t, J=5.9 Hz, 2H), 2.19°–1.88 (m, 2H).

(2) 4-[3-[N-(4-Chlorophenyl)-N-[2-(4-chlorophenylcarbamoyl)ethyl]amino]propoxy]benzoic acid, mp. 212°–213° C.

EXAMPLE 63

(1) 3-(4-Chlorophenylamino)-2-methylpropanol p-Chloroaniline (4 g) and methacyrylic acid (5.40 ml) were heated with stirring at 100° C. for 6 hours and 30 minutes to dissolve. To the reaction solution were added sodium hydroxide (3.76 g) and water (20 ml), and the mixture was heated with stirring at 60° C. for 1 hour. The reaction mixture was cooled and washed with ether 2 times, and neutralized with conc. hydrochloric acid (8.2 ml), and further was extracted with ethyl acetate. The organic layer was washed with water 2 times, and dried over magnesium sulfate, and concentrated under reduced pressure to give an oily product (7.24 g).

Lithium aluminum hydride (3.86 g) was suspended in THF (140 ml) under ice cooling, and thereto was gradually added a solution of the above-mentioned oily product in THF (about 30 ml), and the mixture was stirred at room temperature for 14 hours. Ethyl acetate and a small amount of 1N aqueous sodium hydroxide solution were added to the reaction mixture, and the excess reducing agent was decomposed. The mixture was filtered and concentrated under reduced pressure to give the desired product (5.97 g).

NMR (CDCl$_3$) δppm: 7.10 (d, J=8.8 Hz, 2H), 6.54 (d, J=8.8 Hz, 2H), 3.66–3.58 (m, 2H), 3.13–3.05 (m, 2H), 1.89–1.58 (m, 1H), 0,97 (d, J=6.8 Hz, 3H).

(2) Methyl 4-[3-[N-(4-chlorophenyl)amino]-2-methylpropoxy]benzoate 3-(4-Chlorophenylamino)-2-methylpropanol (3.74 g) and triethylamine (3.90 ml) were dissolved in methylene chloride (60 ml), cooled with ice, and to the mixture was added methanesulfonyl chloride (2.03 ml). The mixture was stirred at room temperature for 15 hours, and concentrated under reduced pressure. To the residue were added water and ethyl acetate, and the mixture was separated into layers. The organic layer was washed with water 2 times and dried over anhydrous magnesium sulfate, and further concentrated under reduced pressure to give oily mesylate compound (5.74 g).

This compound was dissolved in DMF (100 ml) and thereto were added methyl p-hydroxybenzoate (2.85 g) and potassium carbonate (7.76 g), and the mixture was heated with stirring at 90° C. for 16 hours. The reaction mixture was cooled and thereto were added water and ethyl acetate to separate into layers. The organic layer was washed with water 3 times, concentrated under reduced pressure, and the residue was subjected to column chromatography on silica gel and eluted with a mixed solvent of chloroform/methanol [100:1 (v/v)] to give the oily desired product (2.80 g).

NMR (CDCl$_3$) δppm: 7.99 (d, J=9.0 Hz, 2H), 7.10 (d, J=9.0 Hz, 2H), 6.91 (d, J=9.0 Hz, 2H), 6.52 (d, J=9.0 Hz, 2H), 3.96 (d, J=5.9 Hz, 2H), 3.88 (s, 3H), 3.42-3.00 (m, 2H), 2.48-2.12 (m, 1H), 1.12 (d, J=6.8 Hz, 3H).

(3) 4-[3-[N-(4-Chlorophenyl)amino]-2-methylpropoxy]benzoic acid

Methyl 4-[3 [N-[4-chlorophenyl)amino]-2-methylpropoxy]benzoate (2.80 g) was dissolved in methanol (30 ml) and thereto was added a solution of sodium hydroxide (1.00 g) in water (8 ml), and the mixture was heated with stirring at 60° C. for 15 hours. The reaction mixture was cooled and thereto was added conc. hydrochloric acid (2.20 ml), and the mixture was concentrated under reduced pressure. To the residue was added water and it was crushed, and was collected by filtration. The resultant was dissolved in methanol, and filtered. Water (about half volume of the filtrate) was added to the filtrate gradually, and the resulting crystal was collected by filtration to give the desired product (2.16 g). mp. 148°–150° C.

EXAMPLES 64–67

The following compounds were obtained in the same manner as Example 63 by using the proper starting materials.

EXAMPLE 64

(1) 3-(4-Chlorophenylamino)-1-butanol

NMR (CDCl$_3$) δppm: 7.11 (d, J=8.8 Hz, 2H), 6.55 (d, J=8.8 Hz, 2H), 3.86-3.58 (m, 3H), 1.85-1.67 (m, 2H), 1.19 (d, J=5.9 Hz, 3H).

(2) Methyl 4-[3-[N-(4-chlorophenyl)amino]butyl-1-oxy]benzoate

NMR (CDCl$_3$) δppm: 7.96 (d, J=9.0 Hz, 2H), 7.47-7.21 (m, 4H), 6.84 (d, J=9.0 Hz, 2H), 4.19-3.57 (m, 6H), 2.52-1.92 (m, 2H), 1.41 (d, J=6.4 Hz, 3H).

(3) 4-[3-[N-(4-Chlorophenyl)amino]butyl-1-oxy]benzoic acid, mp. 136°–137° C.

EXAMPLE 65

(1) 3-(4-Chlorophenylamino)-2-methyl-1-butanol

NMR (CDCl$_3$) δppm: 7.10 (d, J=8.8 Hz, 2H), 6.55 (d, J=8.8 Hz, 2H), 3.99 (bs, 2H), 3.69-3.46 (m, 1H), 1.90-1.50 (m, 1H), 1.21-0.86 (m, 6H).

(2) Methyl 4-[3-[N-(4-chlorophenyl)amino]-2-methylbutyl-1-oxy]benzoate

NMR (CDCl$_3$) δppm: 7.98 (d, J=8.7 Hz, 2H), 7.12-6.84 (m, 4H), 6.51 (d, J=8.7 Hz, 2H), 4.02-3.88 (m, 5H), 3.79-3.53 (m, 1H), 2.35-2.05 (m, 1H), 1.24-1.01 (m, 6H).

(3) 4-[3-[N-(4-Chlorophenyl)amino]-2-methylbutyl-1-oxy]benzoic acid, mp. 129°–132° C.

EXAMPLE 66

(1) 3-(4-Chlorophenylamino)-1-pentyl alcohol

NMR (CDCl$_3$) δppm: 7.10 (d, J=8.8 Hz, 2H), 6.55 (d, J=8.8 Hz, 2H), 3.85-3.35 (m, 3H), 1.86-1.20 (m, 4H), 0.92 (t, J=7.0 Hz, 3H).

(2) Methyl 4-[3-[N-(4-chlorophenyl)amino]pentyloxy]benzoate

NMR (CDCl$_3$) δppm: 7.97 (d, J=9.0 Hz, 2H), 7.05 (d. J=8.8 Hz, 2H), 6.88 (d, J=8.8 Hz, 2H), 6.50 (d, J=9.0 Hz, 2H), 4.11 (t, J=6.2 Hz, 2H), 3.88 (s, 3H), 3.67-3.30 (m, 1H), 2.30-1.23 (m, 4H), 1.04-0.88 (m, 3H).

(3) 4-[3-[N-(4-Chlorophenyl)amino]pentyl-1-oxy]benzoic acid, mp. 112°–113° C.

EXAMPLE 67

(1) 3-(4-Chlorophenylamino)-1-hexanol

NMR (CDCl$_3$) δppm: 7.10 (d, J=8.8 Hz, 2H), 6.54 (d, J=8.8 Hz, 2H), 3.85-3.49 (m, 3H), 1.90-1.18 (m, 6H), 0.90 (t, J=6.4 Hz, 3H).

(2) Methyl 4-[3-[N-(4-chlorophenyl)amino]hexyloxy]benzoate

NMR (CDCl$_3$) δppm: 7.97 (d, J=9.0 Hz, 2H), 7.15 (d, J=9.0 Hz, 2H), 6.88 (d, J=9.0 Hz, 2H), 6.50 (d, J=9.0 Hz, 2H), 4.10 (t, J=5.9 Hz, 2H), 3.88 (s, 3H), 3.70-3.23 (m, 1H), 2.30-1.74 (m, 2H), 1.66-1.20 (m, 4H), 0.98-0.81 (m, 3H).

(3) 4-[3-[N-(4-Chlorophenyl)amino]hexyl-1-oxy]benzoic acid, mp. 112°–114° C.

EXAMPLE 68

(1) Ethyl 2-(4-chlorophenylamino)-1-cyclopentanecarboxylate p-Chloroaniline (4 g), ethyl 2-oxocyclopentanecarboxylate (4.66 ml) and p-toluenesulfonic acid hydrate (0.66 g) were dissolved in benzene (80 ml), and the mixture was subjected to dehydrating condensation reaction under refluxing for 24 hours, and the mixture was allowed to cool. The insoluble material was removed by filtration, and the filtrate was concentrated under reduced pressure to give an oily product. This oily product was dissolved in absolute methanol (60 ml) and thereto was added sodium cyanoboron hydride (13.2 g) with stirring at room temperature in 10 portions over a period of 11 days. The reaction mixture was cooled with ice and thereto was added conc. hydrochloric acid (21 ml), and the mixture was concentrated under reduced pressure. Water and ethyl acetate were added to the resultant to separate into layers. The organic layer was washed with water 3 tlmes, and concentrated again under reduced pressure. The residue was subjected to column chromatography on silica gel and eluted with a mixed solvent of chloroform/methanol [100:1 (v/v)] to give the oily desired product (3.76 g).

NMR (CDCl$_3$) δppm: 7.10 (d, J=8.8 Hz, 2H), 6.58-6.46 (m, 2H), 4.24-3.87 (m, 3H), 2.31-1.45 (m, 7H), 1.30-1.01 (m, 3H).

(2) 2-(4-Chlorophenylamino)-1-cyclopentanemethanol

Lithium aluminum hydride (1.60 g) was suspended in THF (70 ml) under ice cooling and thereto a solution of ethyl 2-(4-chlorophenylamino)-1-cyclopentanecarboxylate in THF (about 16 ml) was added gradually, and the mixture was stirred at room temperature for 14 hours. Ethyl acetate and a small amount of 1N aqueous sodium hydroxide solution were added to the reaction mixture to decompose the excess reducing agent. The mixture was filtered and concentrated under reduced pressure to give the oily desired product (3.24 g).

NMR (CDCl$_3$) δppm: 7.10 (d, J=9.0 Hz, 2H), 6.56 (d, J=9.0 Hz, 2H), 3.87-3.44 (m, 3H), 2.47-1.17 (m, 7H).

(3) Methyl 4-[2-[N-(4-chloropheny)amino]cyclopentan-1-ylmethoxy]benzoate 2-(4-Chlorophenylamino)-1-cyclopentanemethanol (3.46 g) and triethylamine (6.37 g) were dissolved in methylene chloride (35 ml) and cooled with ice, and thereto was added methanesufonyl chloride (1.66 g), then, the mixture was stirred at room temperature for 22 hours, and concentrated under reduced pressure. Water and ethyl acetate were added to the residue and the mixture was separated into layers. The organic layer was washed with water 2 times and dried over anhydrous magnesium sulfate and concentrated under reduced pressure to give oily mesylate compound (4.22 g).

This compound was dissolved in DMF (90 ml) and thereto were added methyl p-hydroxybenzoate (2.11 g) and potassium carbonate (5.76 g), and the mixture was heated with stirring at 90° C. for 24 hours. The reaction mixture was cooled and thereto were added water and ethyl acetate, and the mixture was separated into layers. The organic layer was washed with water 3 times and concentrated under reduced pressure, and the residue was subjected to column chromatography on silica gel and eluted with a mixed solvent of chloroform/n-hexane [1:1 (v/v)] to give the oily desired product (2.58 g).

NMR (CDCl$_3$) δppm: 7.97 (d, J=9.0 Hz, 2H), 7.09 (d, J=9.0 Hz, 2H), 6.88 (d, J=9.0 Hz, 2H), 6.55 (d, J=9.0 Hz, 2H), 4.01 (d, J=5.9 Hz, 2H), 3.88 (s, 3H), 3.77-3.51 (m, 1H), 2.37-1.27 (m, 7H).

(4) 4-[2-[N-(4-Chlorophenyl)amino]cyclopentan-1-ylmethoxy]benzoic acid

Methyl 4-[2-[N-(4-chlorophenyl)amino]cyclopentan-1-ylmethoxy]benzoate (2.57 g) was dissolved in methanol (40 ml) and thereto was added a solution of sodium hydroxide (0.86 g) in water (8 ml), and the mixture was heated with stirring at 60° C. for 14 hours. The reaction mixture was cooled and thereto was added conc. hydrochloric acid (1.87 ml), then, the mixture was concentrated under reduced pressure. The residue was washed with water and about 50 % aqueous methanol was added thereto, and the mixture was heated. The mixture was allowed to stand, and the resulting crystal was collected by filtration to give the desired product (1.72 g). mp. 153°-156° C.

EXAMPLES 69-71

The following compounds were obtained in the same manner as Example 1 by using the proper starting materials.

EXAMPLE 69

(1) Methyl 4-[3-[N-(4-trifluoromethylphenyl)amino]propoxy]benzoate hydrochloride, mp. 118°-123° C.

(2) 4-[3-[N-(4-Trifluoromethylphenyl)amino]propoxy]benzoic acid, mp. 150°-153° C.

EXAMPLE 70

(1) Methyl 4-[3-[N-(4-iodophenyl)amino]propoxy]benzoate hydrochloride, mp. 152°-154° C.

(2) 4-[3-[N-(4-Iodophenyl)amino]propoxy]benzoic acid, mp. 154°-155° C.

EXAMPLE 71

(1) Methyl 4-[3-(N-phenylamino)propoxy]benzoate, mp. 100°-102° C.

(2) 4-[3-(N-Phenylamino)propoxy]benzoic acid, mp. 147°-148° C.

EXAMPLE 72

The following compound was obtained in the same manner as Example 12 by using the proper starting material.

4-[3-[N-(4-Ethylphenyl)amino]propoxy]benzoic acid, mp. 162°-165° C.

EXAMPLE 73

The following compounds were obtained in the same manner as Example 63 by using the proper starting materials.

(1) 3-(4-Bromophenylamino)-2-methylpropanol

NMR (CDCl$_3$) δppm: 7.24 (d, J=8.8 Hz, 2H), 6.50 (d, J=8.8 Hz, 2H), 3.68-3.60 (m, 2H), 3.15-3.06 (m, 2H), 2.12-1.82 (m, 1H), 0.98 (d, J=6.8 Hz, 3H).

(2) Methyl 4-[3-[N-(4-bromophenyl)amino]-2-methylbenzoate

NMR (CDCl$_3$) δppm: 7.98 (d, J=9.0 Hz, 2H), 7.22 (d, J=9.0 Hz, 2H), 6.48 (d, J=9.0 Hz, 2H), 3.96 (d, J=6.2 Hz, 2H), 3.88 (s, 3H), 3.41-2.92 (m, 2H), 2.49-2.12 (m, 1H), 1.11 (d, J=6.8 Hz, 3H).

(3) 4-[3-[N-(4-Bromophenyl)amino]-2-methylpropoxy]benzoic acid, mp. 164°-167° C.

EXAMPLES 74-75

The following compounds were obtained in the same manner as Example 25 by using the proper starting materials.

EXAMPLE 74

(1) Methyl 4-[3-[N-(4-bromophenyl)-N-methylamino]propoxy]benzoate, mp. 105°-107° C.

(2) 4-[3-[N-(4-Bromophenyl)-N-methylamino]propoxy]benzoic acid, mp. 175°-176° C.

EXAMPLE 75

(1) Methyl 4-[3-[N-(4-chlorophenyl)-N-methylamino]-2-methylpropoxy]benzoate

NMR (CDCl$_3$) δppm: 7.98 (d, J=9.0 Hz, 2H), 7.12 (d, J=9.2 Hz, 2H), 6.89 (d, J=9.0 Hz, 2H), 6.60 (d, J=9.2 Hz, 2H), 3.93-3.88 (m, 5H), 3.63-3.10 (m, 2H), 2.92 (s, 3H), 2.57-2.18 (m, 1H), 1.09 (d, J=6.8 Hz, 3H).

(2) 4-[3-[N-(4-Chlorophenyl)-N-methylamino]-2methylpropoxy]benzoic acid, mp. 154°-155° C.

EXAMPLE 76

(1) Ethyl 2-(4-chlorophenylcarbamoyl)butyrate

Diethyl 2-ethylmalonate (8.76 ml) and p-chloroaniline (4 g) were dissolved by heating at 130° C. for 11 hours, and the mixture was cooled and dissolved in ethyl acetate, and further, the mixture was washed successively with 1N hydrochloric acid, aqueous sodium bicarbonate solution, and water, and concentrated under reduced pressure. The resulting residue was subjected to column chromatography on silica gel and eluted with chloroform to give the oily desired product (6.66 g).

NMR (CDCl$_3$) δppm: 7.51 (d, J=8.8 Hz, 2H), 7.28 (d, J=8.8 Hz, 2H), 4.25 (q, J=7.0 Hz, 2H), 3.29 (t, J=7.6 Hz, 1H), 2.22-1.90 (m, 2H), 1.31 (t, J=7.0 Hz, 3H), 1.01 (t, J=7.3 Hz, 3H).

(2) 3-(4-Chlorophenylamino)-2-ethylpropanol

Lithium aluminum hydride (2.81 g) was suspended in THF (60 ml) and cooled with ice and thereto was added gradually a solution of ethyl 2-(4-chlorophenyl-cabamoyl)butyrate (6.65 g) in THF (about 40 ml), and the mixture was stirred at room temperature for 20 minutes and further heated with stirring for 6 hours under refluxing. To the reaction mixture were added ethyl acetate and a small amount of 1N aqueous sodium hydroxide solution, and the excess reducing agent was decomposed. The resultant was concentrated under reduced pressure, and the residue was extracted by ethyl acetate, filtered, and concentrated again under reduced pressure to give the oily desired product (3.84 g).

NMR (CDCl$_3$) $\delta$ppm: 7.10 (d, J=8.7 Hz, 2H), 6.54 (d, J=8.7 Hz, 2H), 4.23–3.97 m, 1H), 3.87–3.54 (m, 2H), 3.20–3.02 (m, 2H), 1.87–1.61 (m, 1H), 1.56–1.15 (m, 2H), 0.97 (t, J=6.8 Hz, 3H).

The following compounds were obtained respectively in the same manners as Examples 63-(2) and 63-(3) by using the above-mentioned compounds.

(3) Methyl 4-[3-[N-(4-chlorophenyl)amino]-2-ethylpropoxy]benzoate

NMR (CDCl$_3$) $\delta$ppm: 7.99 (d, J=9.0 Hz, 2H), 7.10 (d, J=8.8 Hz, 2H), 6.91 (d, J=8.8 Hz, 2H), 6.52 (d, J=9.0 Hz, 2H), 4.16–3.98 (m, 2H), 3.89 (s, 3H), 3.27–3.05 (m, 2H), 2.27–1.81 (m, 1H), 1.74–1.30 (m, 2H), 1.10 3H).

(4) 4-[3-[N-(4-Chlorophenyl)amino]-2-ethylpropoxy]-benzoic acid, mp. 119°–120° C.

| Preparation 1 | |
|---|---|
| Compound of Example 2 | 200 mg |
| Glucose | 250 mg |
| Water for injection | q.s. |
| Total | 5 ml |

After the compound of Example 2 and glucose were dissolved in water for injection, the solution was poured into a 5 ml ampoule, and after purging with nitrogen, sterilized under pressure at 121° C. for 15 minutes to give an injection preparation having the above composition.

| Preparation 2 | |
|---|---|
| Compound of Example 3 | 100 mg |
| Abicel (trade name, manufactured by Asahi Chemical Industry, Co., Ltd.) | 40 g |
| Corn starch | 30 g |
| Magnesium stearate | 2 g |
| TC-5 (trade name of hydroxypropyle methyl cellulose, manufactured by Shin-Etsu Chemical Co.,Ltd.) | 10 g |
| Polyethlene glycol-6000 | 3 g |
| Castor oil | 40 g |
| Ethanol | 40 g |

The compound of Example 3, Abicel, corn starch and magnesium stearate were mixed and kneaded, and the mixture was tabletted with a pounder (R 10 mm) for sugar coating. The resulting tablets were film-coated with a film coating agent consisting of TC-5, polyethylene glycol-6000, castor oil and ethanol to give a film-coated preparation having the above-mentioned composition.

| Preparation 3 | |
|---|---|
| Compound of Example 4 | 2 g |
| Purified lanolin | 5 g |
| Bleached beeswax | 5 g |
| White vaseline | 88 g |
| Total | 100 g |

White beeswax was heated until it became liquid, and thereto the compound of Example 4, purified lanolin and white vaseline were added. The mixture was heated until it became liquid, and then, stirred until it started to solidify to give an ointment having the above-mentioned composition.

Pharmacological test I

Test of effect on biosynthesis system of sterol or fatty acid by using rat liver slices:

In this test, male Wistar rats (weight; about 200 g) were killed and their livers were taken out and perfused with cold Krebs-Ringer bicarbonate buffer solution (hereinafter referred to KRB), and cut into small slices. Using the small liver slices, the test was carried out in the following manner referring to the following literatures.

Bortz, W. M. and Steele, L. A. (1973), Biochim. Biophys. Acta, 306, 85–94.

Tsujita, Y., Kuroda, M., Shimada, Y., Tanzawa, K., Arai, M., Kaneko, I., Tanaka, M., Masuda, H., Tarumi, C., Watanabe, Y. and Fujii, S. (1986), Biochim. Biophys. Acta, 877, 50–60.

That is to say, the above-mentioned small liver slices (100 mg) were weighed and added into the KRB (1 ml) which contained [1–$^{14}$C] acetic acid (2 $\mu$Ci/2 $\mu$mol) and a prescribed amount of test compounds, and the mixture was reacted with shaking at 37° C. for 2 hours under atmosphere of 95% $O_2$/5% $CO_2$. Thereafter, to the reaction mixture was added 15% solution of sodium hydroxide in ethanol (1 ml), and further heated at 75° C. for 2 hours. After cooling, petroleum ether (2 ml) was added to the mixture, and it was shaken and separated into layers. The petroleum ether layer (upper layer) was extracted. The petroleum ether layer was concentrated to dryness, and thereto digitonin solution (1 ml) was added and sterol was collected in the resulting precipitation fraction. This fraction was washed with diethyl ether and dissolved in acetic acid (1 ml), and the radioactivity of the sample was measured to determine the sterol biosynthesis activity.

On the basis of the value obtained in the control test, in which the above procedure was repeated except that no test compound was used, the concentration ($\mu$M) of the test compound which inhibited 50% of sterol biosynthesis activity was calculated, which was shown as 50% inhibitory concentration.

On the other hand, hydrochloric acid was added into the lower layer obtained by extraction with petroleum ether in the above procedure, and the mixture was extracted with petroleum ether under an acidic condition, and the extract was concentrated, and then, the radioactivity was measured likewise to determine the fatty acid biosynthesis activity. Likewise as above, on the basis of the fatty acid biosynthesis activity obtained in the control test, 50% fatty acid biosynthesis activity inhibitory concentration of the test compounds were determined.

Thus obtained results were showed in the following Table 1.

TABLE 1

| Test sample (Ex. No.) | 50% Inhibitory conc. ($\mu M$) Sterol | Fatty acid |
|---|---|---|
| 1 (3) | 3.88 | 2.40 |
| 2 (2) | 17.86 | 5.41 |
| 3 (2) | 26.28 | 6.05 |
| 4 (2) | 7.59 | 3.11 |
| 5 (2) | 27.79 | 2.75 |
| 6 (2) | 68.99 | 3.39 |
| 8 (2) | 12.62 | 3.12 |
| 10 (2) | 21.18 | 3.44 |
| 11 (2) | 36.48 | 4.43 |
| 12 | 18.21 | 7.48 |
| 13 | 12.98 | 10.46 |
| 14 | 27.96 | 8.22 |
| 15 | 51.99 | 4.71 |
| 16 | 20.55 | 13.64 |
| 17 (2) | 10.84 | 8.72 |
| 18 (2) | 77.12 | 17.0 |
| 19 (2) | 4.51 | 2.05 |
| 20 (2) | 7.19 | 7.22 |
| 22 (2) | 16.51 | 10.22 |
| 24 (2) | 15.47 | 4.49 |
| 25 (2) | 5.01 | 3.39 |
| 26 (2) | 4.27 | 3.26 |
| 27 (2) | 4.97 | 3.56 |
| 28 (2) | 22.50 | 14.55 |
| 29 (2) | 92.10 | 15.62 |
| 30 (2) | 48.45 | 32.56 |
| 39 (2) | 4.50 | 2.30 |
| 63 (2) | 5.30 | 3.31 |

Pharmacological Test II

Test of antilipidemic activity in normal rabbits:

It is generally known that for testing antilipidemic activity of a compound which shows the activity based on the inhibition of cholesterol biosynthesis, it is preferable to test it in rats or dogs [cf. Endo, A., Tsujita, Y., Kuroda, M., and Tanzawa, K.; Biochim. Biophys. Acta, 575, 266–276 (1979)]. Hence, the test of the antilipidemic activity of the present compound was carried out by using rabbits.

In this test, male Japanese white rabbits (weight: 1.9–2.1 kg) were used after they had been subjected to pre-feeding 2 weeks The test compounds were dissolved in chloroform/methanol (3:1) and the mixture was homogeneously blended into CR-2 solid feed (manufactured by Clea Japan Inc.) in the ratio of 0.25%, and then the solvent was removed.

Rabbits were divided into groups (3 rabbits per each group) and were fed with 100–120 g feed (100 g/less than 2.5 kg body weight, 110 g/2.5–3.0 kg body weight, 120 g/more than 3.0 kg body weight) at 9 o'clock every morning for 2 weeks. Before the feeding, blood was taken from ear venula with the lapse of time and at the same time their weight and the uptake of feed were measured. The serum lipids were determined by enzymeassay with an automatic analyzer. The compound of Example 1 (3) was used as the test compound, and after 2 weeks administration, the changing rate of rabbit serum lipids was measured.

As the result, the changing rate of cholesterol was −27.1%, and that of triglyceride was −17.7%.

It is obvious from the above results that the compound of the present invention has the antilipidemic activity in normal rabbits.

We claim:

1. A compound of the formula

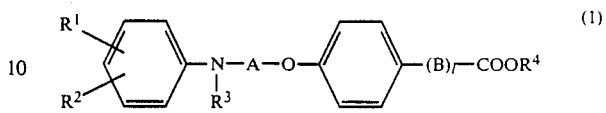

wherein $R^1$ and $R^2$ are each hydrogen atom, a halogen atom, a $C_1$–$C_6$ alkyl group, a $C_1$–$C_6$ alkyl group having a halogen atom, a $C_3$–$C_8$ cycloalkyl group, a nitro group, a $C_1$–$C_6$ alkoxy group, of a phenoxy group having a substituent of a halogen atom, or both groups $R^1$ and $R^2$ form a $C_1$–$C_4$ alkylenedioxy group which bond to adjacent carbon atoms;

$R^3$ is hydrogen atom, a $C_1$–$C_6$ alkyl group which may be substituted by a carboxyl group, or a $C_2$–$C_6$ alkenyl group;

$R^4$ is hydrogen atom or a $C_1$–$C_6$ alkyl group;

A is a $C_1$–$C_6$ alkylene group or a $C_2$–$C_6$ alkenylene group;

B is a $C_1$–$C_6$ alkylene group or a $C_2$–$C_6$ alkenylene group;

$l$ is 0 or 1, or a pharmaceutically acceptable salt thereof.

2. The compound according to claim 1, wherein A is a $C_3$–$C_4$ alkylene group, $R^1$ is hydrogen atom, $R^2$ is chlorine atom or bromine atom.

3. The compound according to claim 2, wherein $l$ is 0.

4. The compound according to claim 3, wherein $R^3$ is hydrogen atom.

5. The compound according to claim 3, wherein $R^3$ is a $C_1$–$C_6$ alkyl group.

6. The compound according to claim 2, wherein $l$ is 1.

7. The compound according to claim 6, wherein $R^3$ is hydrogen atom.

8. The compound according to claim 2, which is selected from the following compounds:

4-[3-[N-(4-chlorophenyl)amino]propoxy]benzoic acid,

4-[3-[N-(4-chlorophenyl)amino]propoxy]-α-methylcinnamic acid,

4-[3-[N-(4-chlorophenyl)-N-methylamino]propoxy]benzoic acid, and

4-[3-[N-(4-bromophenyl)amino]propoxy]benzoic acid.

9. A hypolipidemic pharaceutical composition which comprises an effective hypolipidemic amount of a compound or salt as defined in claim 1 in admixture with a conventional pharmaceutically acceptable carrier or diluent.

10. A method for the treatment of hyperlipidemia which comprises administering an effective hypolipidemic amount of a compound or salt as defined in claim 1 to a patient in need thereof.

* * * * *

UNITED STATES PATENT AND TRADEMARK OFFICE
CERTIFICATE OF CORRECTION

PATENT NO. : 4,999,378
DATED : March 12, 1991
INVENTOR(S) : Setsuro FUJII et al.

It is certified that error appears in the above-identified patent and that said Letters Patent is hereby corrected as shown below:

Title page, column 1, item [30], after second entry, insert

--Oct. 20, 1988 [WO] PCT Int'l Appl. PCT/JP88/01065--.

Signed and Sealed this

Eighth Day of September, 1992

Attest:

DOUGLAS B. COMER

Attesting Officer

Acting Commissioner of Patents and Trademarks